United States Patent
Goldberg et al.

(10) Patent No.: US 10,456,356 B2
(45) Date of Patent: *Oct. 29, 2019

(54) USE OF ENCAPSULATED CELL THERAPY FOR TREATMENT OF OPHTHALMIC DISORDERS

(71) Applicant: Neurotech USA, Inc., Cumberland, RI (US)

(72) Inventors: Jeffrey Louis Goldberg, San Diego, CA (US); Cahil McGovern, North Kingstown, RI (US); Weng Tao, Lincoln, RI (US); Konrad Kauper, Sutton, MA (US)

(73) Assignee: Neurotech USA, Inc., Cumberland, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,790

(22) Filed: May 27, 2016

(65) Prior Publication Data

US 2016/0346197 A1 Dec. 1, 2016

Related U.S. Application Data

(60) Provisional application No. 62/167,213, filed on May 27, 2015.

(51) Int. Cl.
| | | |
|---|---|---|
| A61K 9/00 | (2006.01) | |
| A61K 38/19 | (2006.01) | |
| A61K 35/30 | (2015.01) | |
| A61K 38/18 | (2006.01) | |
| A61K 38/20 | (2006.01) | |
| A61K 38/21 | (2006.01) | |
| A61F 9/00 | (2006.01) | |
| A61K 9/48 | (2006.01) | |

(52) U.S. Cl.
CPC .......... *A61K 9/0051* (2013.01); *A61F 9/0017* (2013.01); *A61K 9/4816* (2013.01); *A61K 35/30* (2013.01); *A61K 38/185* (2013.01); *A61K 38/19* (2013.01); *A61K 38/2066* (2013.01); *A61K 38/212* (2013.01); *A61K 38/215* (2013.01)

(58) Field of Classification Search
USPC ........................................................ 424/425
See application file for complete search history.

(56) References Cited

U.S. PATENT DOCUMENTS

| | | |
|---|---|---|
| 3,615,024 A | 10/1971 | Michaels |
| 4,409,331 A | 10/1983 | Lim |
| 4,652,833 A | 3/1987 | Batts |
| 4,744,933 A | 5/1988 | Rha et al. |
| 4,892,538 A | 1/1990 | Aebischer et al. |
| 4,968,733 A | 11/1990 | Muller et al. |
| 4,976,859 A | 12/1990 | Wechs |
| 4,997,929 A | 3/1991 | Collins et al. |
| 5,002,661 A | 3/1991 | Chick et al. |
| 5,141,856 A | 8/1992 | Collins et al. |
| 5,156,844 A | 10/1992 | Aebischer et al. |
| 5,158,881 A | 10/1992 | Aebischer et al. |
| 5,283,138 A | 2/1994 | Ferrando |
| 5,283,187 A | 2/1994 | Aebischer et al. |
| 5,284,761 A | 2/1994 | Aebischer et al. |
| 5,364,769 A | 11/1994 | Rosenthal |
| 5,453,361 A | 9/1995 | Yancopoulos et al. |
| 5,512,600 A | 4/1996 | Mikos et al. |
| 5,550,050 A | 8/1996 | Holland et al. |
| 5,639,275 A | 6/1997 | Baetge et al. |
| 5,653,688 A | 8/1997 | Mills et al. |
| 5,653,975 A | 8/1997 | Baetge et al. |
| 5,713,887 A | 2/1998 | Mills et al. |
| 5,738,673 A | 4/1998 | Mills et al. |
| 5,762,798 A | 6/1998 | Wenthold et al. |
| 5,932,460 A | 8/1999 | Mills et al. |
| 6,123,700 A | 9/2000 | Mills et al. |
| 6,303,136 B1 | 10/2001 | Li et al. |
| 6,361,771 B1 * | 3/2002 | Tao ...................... A61K 9/0024 424/93.21 |
| 6,627,422 B1 | 9/2003 | Li et al. |
| 6,653,687 B1 | 11/2003 | Yamazaki |
| 7,115,257 B1 * | 10/2006 | Tao ...................... A61K 9/0024 424/93.2 |

(Continued)

FOREIGN PATENT DOCUMENTS

| | | |
|---|---|---|
| WO | WO 91/00119 A1 | 1/1991 |
| WO | WO 92/03327 A1 | 3/1992 |

(Continued)

OTHER PUBLICATIONS

Aebischer, P. et al., "Transplantation in Humans of Encapsulated Xenogenetic Cells without Immunosuppression," *Division of Surgical Research, CHUV, University of Lausanne Medical School* (1994) 58 (11): 1275-1277.

Baetge, E. et al., "Complete nucleotide and deduced amino acid sequence of bovine phenylethanolamine N-methyltransferase: Partial amino acid homology with rat tyrosine hydroxylase," *Proceedings of the National Academy of Sciences* (1986) 83: 5454-5458.

Boyd, Z.S. et al., "Interleukin-10 Receptor Signaling through STAT-3 Regulates the Apoptosis of Retinal Ganglion Cells in Response to Stress," *Investigative Ophthalmology & Visual Science* (2003) 44 (12): 5206-5211.

(Continued)

*Primary Examiner* — Devang K Thakor
(74) *Attorney, Agent, or Firm* — Cooley LLP; Ivor R. Elrifi; Matthew Pavao

(57) ABSTRACT

Described herein are methods and devices for the long term treatment of ophthalmic disorders. Also disclosed are encapsulated cell therapy (ECT) devices that secrete a biologically active molecule and methods for using the same for the treatment of various kinds of ophthalmic disorders, including retinitis pigmentosa, geographic atrophy (dry age-related macular degeneration), glaucoma and/or macular telangiectasia.

9 Claims, 22 Drawing Sheets

(56) References Cited

U.S. PATENT DOCUMENTS

| | | | |
|---|---|---|---|
| 9,265,814 B2* | 2/2016 | Kauper | A61K 9/0048 |
| 2011/0236457 A1* | 9/2011 | Kauper | A61K 9/0048 |
| | | | 424/424 |
| 2012/0141573 A1 | 6/2012 | Ling et al. | |
| 2015/0073381 A1 | 3/2015 | Kauper et al. | |
| 2018/0055766 A1 | 3/2018 | McGovern et al. | |

FOREIGN PATENT DOCUMENTS

| | | |
|---|---|---|
| WO | WO 92/19195 A1 | 11/1992 |
| WO | WO 93/00128 A1 | 1/1993 |
| WO | WO 93/03901 A1 | 3/1993 |
| WO | WO 93/06116 A1 | 4/1993 |
| WO | WO 95/05452 A2 | 2/1995 |
| WO | WO 95/30686 A1 | 11/1995 |
| WO | WO 96/02646 A2 | 2/1996 |
| WO | WO 98/05304 A1 | 2/1998 |
| WO | WO 99/52573 A1 | 10/1999 |
| WO | WO 2007/078922 A2 | 7/2007 |
| WO | WO 2011/044216 A1 | 4/2011 |
| WO | WO 2012/075184 A2 | 6/2012 |
| WO | WO 2015/038669 A9 | 3/2015 |

OTHER PUBLICATIONS

Christenson, L., Ph.D. "Polymer-encapsulated thymic stomal tissue: Biocompatibility, procurement and functional studies," *Brown University* (1989) Thesis: 1-119.

Christenson, L. et al., "Tissue reaction to intraperitoneal polymer implants: Species difference and effects of corticoid and doxorubicin," *Journal of Biomedical Materials Research* (1989) 23: 705-718.

Chun, L. and Patterson, P., "Role of Nerve Growth Factor in the Development of Rat Sympathetic Neurons in Vitro," *Journal of Cell Biology* (1977) 75: 694-704.

Colton, C.K., "Engineering challenges in cell-encapsulation technology," *Trends in Biotechnology* (1996) 14: 158-162.

Colton, C.K. et al., "Hemodialysis: Physical Principles and Technical Considerations," *The Kidney* Second Edition (1981) Chapter 47: 2425-2489.

Dionne, K. et al., "1993 Abstracts," *American Society for Artificial Organs* (1993) 22 (39): 99.

Dunn, K.C. et al., "ARPE-19, A Human Retinal Pigment Epithelial Cell Line with Differentiated Properties," *Experimental Eye Research* (1996) 62: 155-169.

Dunn, K.C. et al., "Use of the ARPE-19 Cell Line as a Model of RPE Polarity: Basolateral Secretion of FGF5," *Investigative Ophthalmology & Visual Science* (1998) 39 (13): 2744-2749.

Faithfull, N.S., "Fluorocarbons," *Anaesthesia* (1987) 42: 234-242.

Finnemann, S.C. et al., "Phagocytosis of rod outer segments by retinal pigment epithelial cells requires αvβ5 integrin for binding but not for internalization," *Proceedings of the National Academy of Sciences* (1997) 94: 12932-12937.

GenBank Accession No. AF063658, May 16, 1998.
GenBank Accession No. BC032224, Jul. 15, 2006.
GenBank Accession No. NM-006206, Feb. 21, 2016.
GenBank Accession No. P26441.1. Jul. 6, 2016.
GenBank Accession No. U01134, Feb. 2, 1994.
GenBank Accession No. X60477.1, Nov. 14, 2006.
*Genetic Technology News*, (1993) 13 (1): 1-3.

Handa, J.T. et al., "The Advanced Glycation Endproduct Pentosidine Induces the Expression of PDGF-B in Human Retinal Pigment Epithelial Cells," *Experimental Eye Research* (1998) 66: 411-419.

He Yang, C. et al., "IFNα/β promotes cell survival by activating NF-κB," *Proceedings of the National Academy of Sciences* (2000) 97 (25): 13631-13636.

Holtkamp, G.M. et al., "Polarized secretion of IL-6 and IL-8 retinal pigment epithelial cells," *Clinical & Experimental Immunology* (1998) 112: 34-43.

Kauper, K. et al., "Two-Year Intraocular Delivery of Ciliary Neurotrophic Factor by Encapsulated Cell Technology Implants in Patients with Chronic Retinal Degenerative Diseases," *Investigative Ophthalmology & Visual Science* (2012) 53 (12): 7484-7491.

Krieglstein, K. et al., "TGF-β and the regulation of neuron survival and death," *Journal of Physiology* (2002) 96 (1-2): 25-30.

Lacy, P.E. et al., "Maintenance of Normoglycemia in Diabetic Mice by Subcutaneous Xenografts of Encapsulated Islets," *Science* (1991) 254: 1782-1784.

Li, Y. et al., "CNTF Induces Regeneration of Cone Outer Segments in a Rat Model of Retinal Degeneration," *PLoS One* (2010) 5 (3): e9495.

Li, R. et al., "CNTF Mediates Neurotrophic Factor Secretion and Fluid Absorption in Human Retinal Pigment Epithelium," *PLoS One* (2011) 6 (9): e23148.

Lim, F. et al., "Microencapsulated Islets as Bioartificial Endocrine Pancreas," *Science* (1980) 210: 908-910.

Lipton, S. et al., "Acidic fibroblast growth factor enhances regeneration of processes by postnatal mammalian retinal ganglion cells in culture," *Proceedings of the National Academy of Sciences* (1988) 85: 2388-2392.

Lysaght, M.J. et al., "Recent Progress in Immunoisolated Cell Therapy," *Journal of Cellular Biochemistry* (1994) 56: 196-203.

Maidji, E. et al., "Accessory Human Cytomegalovirus Glycoprotein US9 in the Unique Short Component of the Viral Genome Promotes Cell-to-Cell Transmission of Virus in Polarized Epithelial Cells," *Journal of Virology* (1996) 70: 8402-8410.

Meijis, M. et al., "Basic Fibroblast Growth Factor Promotes Neuronal Survival but Not Behavioral Recovery in the Transected and Schwann Cell Implanted Rat Thoracic Spinal Cord," *Journal of Neurotrauma* (2004) 21 (10): 1415-1430.

NASA Tech Briefs: MSC-21480, 14 (9), Sep. 1990.
NASA Tech Briefs: NPO-17517, 15 (1), Jan. 1991.

Sattler, M.B. et al., "Effects of interferon-beta-1a on neuronal survival under autoimmune inflammatory conditions," *Experimental Neurology* (2006) 201 (1): 172-181.

Scharp, D. W. et al., "Islet Immuno-isolation: The Use of Hybrid Artificial Organs to Prevent Islet Tissue Rejection," *World Journal of Surgery* (1984) 8: 221-229.

Siliprandi, R. et al., "Never Growth Factor Promotes Functional Recovery of Retinal Ganglion Cells After Ischemia," *Investigative Ophthalmology & Visual Science* (1993) 34 (12): 3232-3245.

Southern, P.J., "Mammalian Cell Transformation with SV40 Hybrid Plasmid Vectors," In Vitro (1981) 18: 315.

Southern P.J. and Berg, P., "Transformation of Mammalian Cells to Antibiotic Resistance with a Bacterial Gene Under Control of the SV40 Early Region Promoter," *Journal of Molecular and Applied Genetics* (1982) 1: 327-341.

Sun, A.M., "Microencapsulation of Pancreatic Islet Cells: A Bioartificial Endocrine Pancreas," *Methods in Enzymology* (1988) 137: 575-579.

Suzuki, M. et al., "GDNF Secreting Human Neural Progenitor Cells Protect Dying Motor Neurons, but Not Their Projection to Muscle, in a Rat Model of Familial ALS," *PLoS One* (2007) 2(8): e689.

Wilson, D.F. et al., "The Oxygen Dependence of Mitochondrial Oxidative Phosphorylation Measured by a New Optical Method for Measuring Oxygen Concentration," *The Journal of Biological Chemistry* (1988) 263 (6): 2712-2718.

An E. et al. "Effect of TNF-α on human ARPE-19-secreted proteins" *Molecular Vision* (2008), vol. 14, p. 2292-2303.

Charters, L. "5-year macular telangiectasia type 2 project ongoing", *Opthalmology Times*, (2011), 4 pages.

Adams et al., "Glaucoma—Next Generation Therapeutics: Impossible to Possible", Pharm Res. (2018), vol. 36, No. 2, p. 25.

Birch et al., "Randomized Trial of Ciliary Neurotrophic Factor Delivered by Encapsulated Cell Intraocular Implants for Retinitis Pigmentosa", American Journal of Ophthalmology (2013), vol. 156, No. 2, p. 283-292.

Birch et al. "Long-term Follow-up of Patients With Retinitis Pigmentosa Receiving Intraocular Ciliary Neurotrophic Factor Implants", Am J Ophthalmol. (2016), vol. 170, p. 10-14.

Bucher et al., "CNTF Attenuates Vasoproliferative Changes Through Upregulation of SOCS3 in a Mouse-Model of Oxygen-Induced Retinopathy", Investigative Ophthalmology & Visual Science, (2016), vol. 57, No. 10, p. 4017-4026.

Chew et al, "Global Connections to Study Idiopathic Macular Telangiectasia Type 2", Retina, (2018), vol. 38, Suppl 1, p. S3-S7.

(56) References Cited

OTHER PUBLICATIONS

Dittrich et al., "Ciliary Neurotropic Factor: Pharmacokinetics and Acute-Phase Response in Rat", Ann Neurol (1994), vol. 35, No. 2, p. 151-163.

Guymer et al., "Neuroprotection in glaucoma: recent advances and clinical translation", Clinical and Experimental Ophthalmology, (2019), vol. 47, No. 1, p. 88-105.

Haider et al., "Mutation of a nuclear receptor gene, NR2E3, causes enhanced S cone syndrome, a disorder of retinal cell fate", Nature Genetics, (2000), vol. 24, No. 2, p. 127-131.

Haider et al., "Excess cone cell proliferation due to lack of a functional NR2E3 causes retinal dysplasia and degeneration in rd7/rd7 mice", Human Molecular Genetics, (2001), vol. 10, No. 16, p. 1619-1626.

Harrison L. "Cell therapy shows promise in glaucoma", Ophthalmology Times, 2019. Retrieved online: https://www.opthalmologytimes.com/glaucoma-360/cell-therapy-shows-promise-glaucoma.

Issa C. et al., "Macular telangiectasia type 2", Progress in Retinal and Eye Research, (2013), vol. 34, p. 49-77.

Issa C. et al. "Monthly Ranibizumab for Nonproliferative Macular Telangiectasia Type 2: A 12-Month Prospective Study", Am J Ophthalmol. (2011), vol. 151, No. 5, p. 876-886.

Lipinski et al., "CNTF Gene Therapy Confers Lifelong Neuroprotection in a Mouse Model of Human Retinitis Pigmentosa", Molecular Therapy, (2015), vol. 23, No. 8, p. 1308-1319.

Marangoni et al., "Intravitreal Ciliary Neurotrophic Factor Transiently Improves Cone-Mediated Function in a CNGB3-/- Mouse Model of Achromatopsia", Investigative Ophthalmology & Visual Science, (2015), vol. 56, No. 11, p. 6810-6822.

Miller et al., "Toxicity and tolerability of recombinant human ciliary neurotrophic factor in patients with amyotrophic lateral sclerosis", Neurology (1996), vol. 47, No. 50, p. 1329-1331.

Nucci et al. "Neuroprotective agents in the management of glaucoma", Eye, (2018), vol. 32, p. 938-945.

Powner et al., "Perifoveal Müller Cell Depletion in a Case of Macular Telangiectasia Type 2", Ophthalmology (2010), vol. 117, No. 12, p. 2407-2416.

Roller et al., "Intravitreal bevacizumab for treatment of proliferative and nonproliferative type 2 idiopathic macular telangiectasia", Retina, (2011), vol. 31, No. 9, p. 1848-1855.

Scerri et al., "Genome-wide analyses identify common variants associated with macular telangiectasia type 2", Nature Genetics, (2017), vol. 49, No. 4, p. 559-567.

Shen et al., "Conditional Müller Cell Ablation Causes Independent Neuronal and Vascular Pathologies in a Novel Transgenic Model", The Journal of Neuroscience, (2012), vol. 32, No. 45, p. 15715-15727.

Sieving P.A. "Ciliary neurotrophic factor (CNTF) for human retinal degeneration: phase I trial of CNTF delivered by encapsulated cell intraocular implants", PNAS, (2006), vol. 103, No. 10, p. 3896-3901.

Tariot et al., "Memantine Treatment in Patients with Moderate to Severe Alzheimer Disease Already Receiving Donepezil", JAMA (2004), vol. 291, No. 3, p. 317-324.

Weinreb et al., "Oral Memantine for the Treatment of Glaucoma", American Academy of Opthalmology, (2018), vol. 125, No. 12, p. 1874-1885.

Zein et al., "CNGB3-Achromatopsia Clinical Trial With CNTF: Diminished Rod Pathway Responses With No Evidence of Improvement in Cone Function", Investigative Ophthalmology & Visual Science, (2014), vol. 55, No. 10, p. 6301-6308.

Zeiss et al., "CNTF induces dose-dependent alterations in retinal morphology in normal and rcd-1 canine retina", Experimental Eye Research, (2006), vol. 82, No. 3, p. 395-404.

\* cited by examiner t=4.12; P=0.006

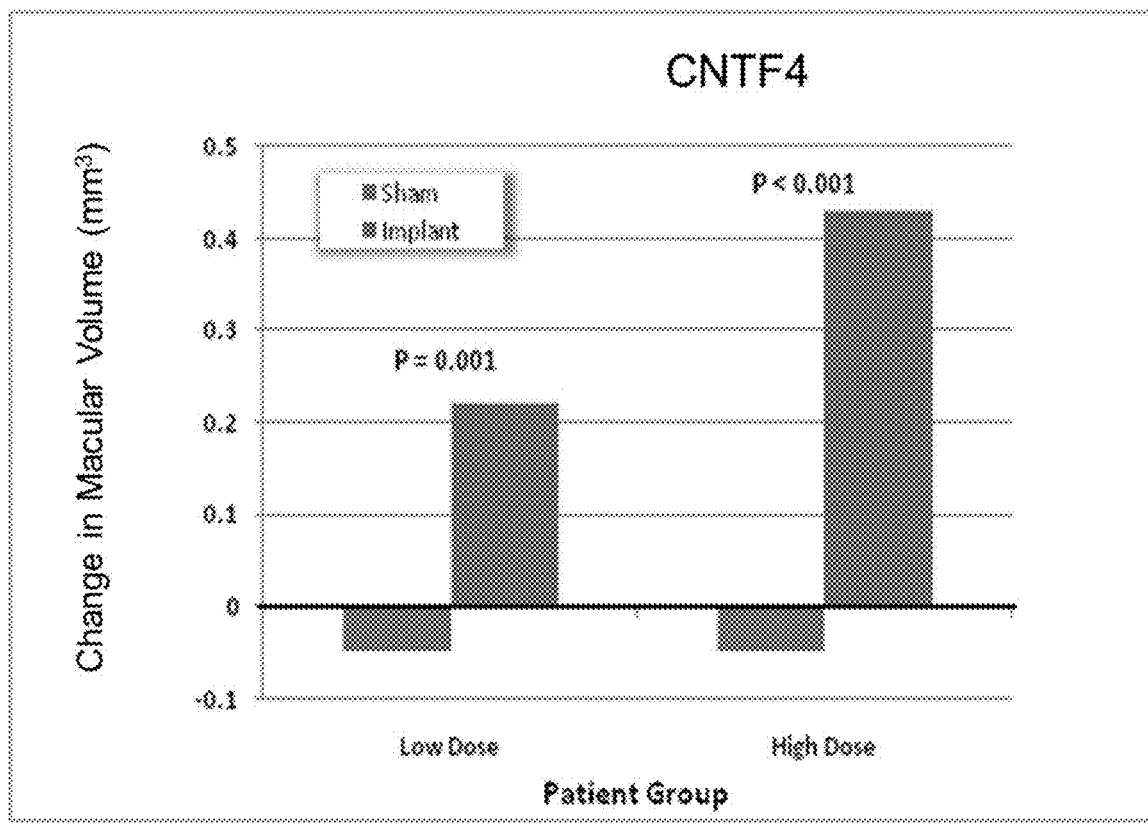

t=1.5; P=0.18

4 have wider EZ in treated eye
2 no difference
1 has wider EZ in sham eye

FIGURE 18
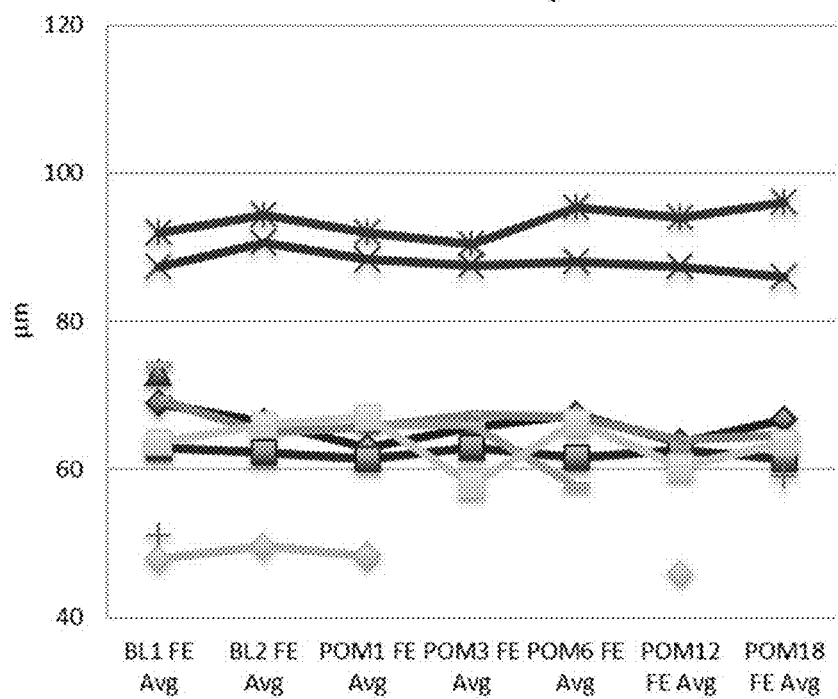
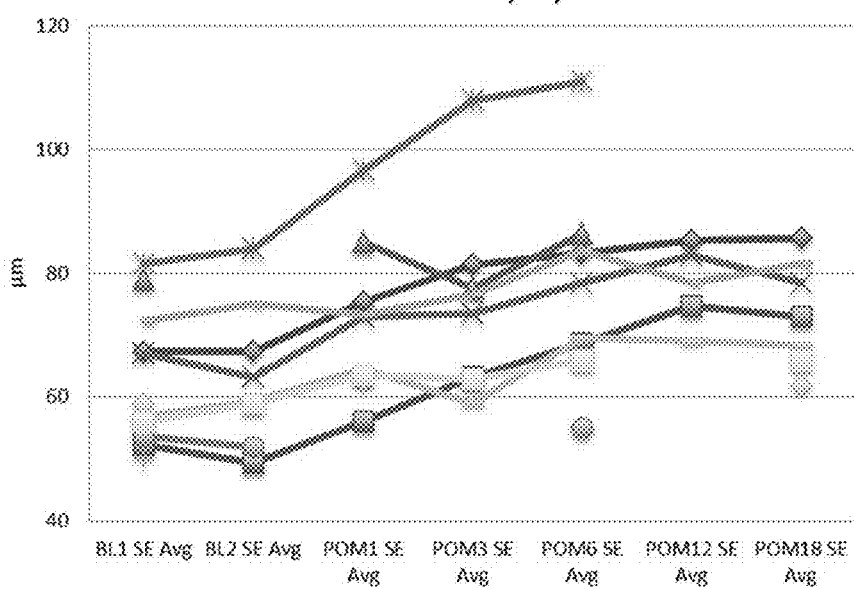

USE OF ENCAPSULATED CELL THERAPY FOR TREATMENT OF OPHTHALMIC DISORDERS

RELATED APPLICATIONS

This application claims priority to U.S. Application No. 62/167,213, filed May 27, 2015, which is herein incorporated by reference in its entirety.

FIELD OF THE INVENTION

The present invention relates generally to the field of encapsulated cell therapy.

BACKGROUND OF THE INVENTION

Many clinical conditions, deficiencies, and disease states can be remedied or alleviated by supplying to the patient one or more biologically active molecules produced by living cells or by removing from the patient deleterious factors which are metabolized by living cells. In many cases, these molecules can restore or compensate for the impairment or loss of organ or tissue function. Accordingly, many investigators have attempted to reconstitute organ or tissue function by transplanting whole organs, organ tissue, and/or cells, which provide secreted products or affect metabolic functions. However, while such transplantation can provide dramatic benefits, it is limited in its application by the relatively small number of organs that are suitable and available for grafting. Moreover, in general, transplantation patients must be immunosuppressed in order to avert immunological rejection of the transplant, which results in loss of transplant function and eventual necrosis of the transplanted tissue or cells. Likewise, in many cases, the transplant must remain functional for a long period of time, even for the remainder of the patient's lifetime. It is both undesirable and expensive to maintain a patient in an immunosuppressed state for a substantial period of time.

One example where additional effective therapies are still needed are vision-threatening disorders of the eye. One major problem in treatment of such diseases is the inability to deliver therapeutic agents into the eye, due to the presence of the blood-retinal barrier, as well as the inability to maintain them there at therapeutically effective concentrations.

Many growth factors have shown promise in the treatment of ocular diseases. For example, BDNF and CNTF have been shown to slow degeneration of retinal ganglion cells and decrease degeneration of photoreceptors in various animal models. See, e.g., Genetic Technology News, vol. 13, no. 1 (January 1993). Additionally, nerve growth factor has been shown to enhance retinal ganglion cell survival after optic nerve section and has also been shown to promote recovery of retinal neurons after ischemia. See, e.g., Siliprandi, et al., Invest. Ophthalmol. & Vis. Sci., 34, pp. 3232-3245 (1993). More recently, antibody scaffold based biologics have been designed and used for eye disorders including, for example, full antibodies (e.g., Bevacizumab) and antibody scaffold Fab fragments (e.g., Ranibizumab), and immunoglobulin Fc (e.g., Aflibercept).

A desirable alternative to transplantation procedures is the implantation of cells or tissues within a physical barrier which will allow diffusion of nutrients, metabolites, and secreted products, but will block the cellular and molecular effectors of immunological rejection. A variety of devices which protect tissues or cells producing a selected product from the immune system have been explored. See, e.g., U.S. Pat. No. 5,158,881; WO92/03327; WO91/00119; and WO93/00128, each of which is incorporated herein by reference in its entirety. These devices include, for example, extravascular diffusion chambers, intravascular diffusion chambers, intravascular ultrafiltration chambers, and implantation of microencapsulated cells. See Scharp, D. W., et al., World J. Surg., 8, pp. 221-9 (1984); Lim et al., Science 210: 908-910 (1980); Sun, A. M., Methods in Enzymology 137: 575-579 (1988); WO 93/03901; and U.S. Pat. No. 5,002,661. The use of such devices would alleviate the need to maintain the patient in an immunosuppressed state. However, none of these approaches have been satisfactory for providing long-term transplant function.

Thus, methods of delivering appropriate quantities of needed substances, such as, for example, neurotrophic factors, anti-angiogenic factors, anti-inflammatory factors, enzymes, hormones, and/or other factors, or of providing other needed metabolic functions, to the eye or other parts of the body for an extended period of time are needed.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present specification, including definitions, will control. In addition, the materials, methods, and examples are illustrative only and are not intended to be limiting. Other features and advantages of the invention will be apparent from the following detailed description and claim.

SUMMARY OF THE INVENTION

Provided herein are methods of treating an ophthalmic disorder in a patient suffering therefrom by implanting into an eye of the patient a biocompatible capsule containing a) a core containing a cellular source of a biologically active molecule and b) a semi-permeable membrane surrounding the core, wherein the membrane permits the diffusion of the biologically active molecule therethrough, wherein the ophthalmic disorder is characterized by aberrant angiogenesis, inflammation, retinal degeneration, or any combination thereof, and wherein said biocompatible device produces therapeutically effective amounts of the biologically active molecule for at least 12 months (e.g., at least 13 months, at least 14 months, at least 15 months, at least 16 months, at least 17 months, at least 18 months, at least 19 months, at least 20 months, at least 21 months, at least 22 months, at least 23 months, at least two years, or more) post implantation.

Also provided herein is a cellular source of a biologically active molecule for use in treating an ophthalmic disorder, wherein the cellular source of biologically active molecule is present in a core of a biocompatible capsule, wherein the biocompatible capsule further comprises a semi-permeable membrane surrounding the core, and wherein the semi-permeable membrane permits the diffusion of the biologically active molecule therethrough. That is, there is provided a biocompatible capsule containing a) a core containing a cellular source of a biologically active molecule and b) a semi-permeable membrane surrounding the core, wherein the semi-permeable membrane permits the diffusion of the biologically active molecule therethrough, and wherein the cellular source of a biologically active molecule is for use in treating an ophthalmic disorder. The ophthalmic disorder is characterized by aberrant angiogenesis, inflammation, retinal degeneration, or any combination thereof. The biocompatible device produces therapeutically effective amounts of the biologically active molecule for at least 12 months (e.g., at least 13 months, at least 14 months, at least 15 months, at least 16 months, at least 17 months, at least 18 months, at least 19 months, at least 20 months, at least 21 months, at least 22 months, at least 23 months, at least 2 years or more) after implantation into an eye of a patient suffering from an ophthalmic disorder.

For example, the cellular source of the biologically active molecules is between $0.5-1\times10^6$ ARPE-19 cells that are genetically engineered to secrete the biologically active molecule.

The ophthalmic disorder can be glaucoma; retinitis pigmentosa (RP); geographic atrophy or age related macular degeneration (AMD), or macular telangiectasia.

Those skilled in the art will recognize that when the ophthalmic disorder is glaucoma, the treating improves optic nerve regeneration; preserves or improves visual field acuity, or Garway-Heath total deviation; preserves or improves the ganglion cell complex and/or the thickness of the outer retinal layer; preserves or improves the retinal fiber layer; and/or any combinations thereof. For example, the preservation or improvement of visual field sensitivity or contrast sensitivity corresponds with the preservation or improvement of the anatomical structure of the retina.

When the ophthalmic disorder is RP, the treating improves visual acuity, increases macular volume, increases retinal thickness, and/or any combinations thereof.

When the ophthalmic disorder is geographic atrophy or age related macular degeneration (AMD), the treating stabilizes vision loss in a subject, decreases loss of best corrected visual acuity, decreases geographic atrophy, and/or any combinations thereof. Alternatively (or additionally), the treating may increase best corrected visual acuity.

The capsule can be configured as a hollow fiber or a flat sheet.

In some embodiments, the capsule is an implantable cell culture device containing two or more (i.e., 2, 3, 4, 5, 6, 7, 8, 9, 10, 11, 12, 13, 14, 15, 16, 17, 18, 19, 20, or more) individual chambers. (See PCT/US2014/055028, which is incorporated herein by reference in its entirety). In such devices, each individual chamber contains a core that contains a therapeutically effective amount of one or more biologically active molecules and a semi-permeable membrane surrounding the core, wherein the membrane permits the diffusion of biologically active molecule(s) there through it.

Any of the capsules described herein can be implanted (or are suitable for implantation) in the vitreous, in the aqueous humor, in the periocular space, in the anterior chamber, in the posterior chamber, or in the Subtenon's space.

The core of the capsules described herein may further contain a matrix disposed within the semipermeable membrane. For example, the matrix may contain a plurality of monofilaments, wherein said monofilaments are a) twisted into a yarn or woven into a mesh or b) twisted into a yarn that is in non-woven strands, and wherein the cells are distributed thereon. The monofilaments may be made from a biocompatible material selected from the group consisting of acrylic, polyester polyethylene, polypropylene, polyacrylonitrile, polyethylene terephthalate, nylon, polyamides, polyurethanes, polybutester, silk cotton, chitin, carbon, and biocompatible metals. By way of non-limiting example, the monofilaments can be made from polyethylene terephthalate (PET) fibers that comprise between 40-85% of the internal volume of the device.

The biologically active molecule is a cytokine. By way of non-limiting example, the cytokine can be selected from the group consisting of CNTF, BDNF, TGF-β, GDNF, NGF, bFGF, aFGF, IL-1β, IL-10, IFN-β, IFN-α, and/or VEGF inhibitors.

In one embodiment, the cytokine is CNTF. The therapeutically effective amount of CNTF is between 50 pg/eye/day and 500 ng/eye/day (e.g. 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 35.0, 40.0, 45.0, 50.0, 60.0, 70.0, 80.0, 90.0, 100.0, 110.0, 120.0, 130.0, 140.0, 150.0, 160.0, 170.0, 180.0, 190.0, 200.0, 210.0, 220.0, 230.0, 240.0, 250.0, 260.0, 270.0, 280.0, 290.0, 300.0, 310.0, 320.0, 330.0, 340.0, 350.0, 360.0, 370.0, 380.0, 390.0, 400.0, 410.0, 420.0, 430.0, 440.0, 450.0, 460.0, 470.0, 480.0, 490.0, or 500.0 ng/eye/day). For example, the therapeutically effective amount of CNTF is 0.1 ng/eye/day and 50 ng/eye/day.

Also provided are implantable cell culture devices containing a) a core containing a cellular source of a biologically active molecule; and b) a semi-permeable membrane surrounding the core, wherein the membrane permits the diffusion of the biologically active molecule therethrough, wherein the device secretes between 0.1 and 20 ng/day of the biologically active molecule upon implantation; and wherein secretion of the biologically active molecule at therapeutically effective levels is maintained for at least 12 months (e.g., at least 13 months, at least 14 months, at least 15 months, at least 16 months, at least 17 months, at least 18 months, at least 19 months, at least 20 months, at least 21 months, at least 22 months, at least 23 months, at least two years, or more) post-implantation. For example, the cellular source of the biologically active molecules is between $0.5-1\times10^6$ ARPE-19 cells that are genetically engineered to secrete the biologically active molecule (e.g., CNTF).

In embodiments, any of the devices described herein can secrete between 0.1 and 20 ng/day of CNTF upon implantation and between 0.1-0.4 ng/day of CNTF at explant following implantation for at least 12 months (e.g. at least 13 months, at least 14 months, at least 15 months, at least 16 months, at least 17 months, at least 18 months, at least 19 months, at least 20 months, at least 21 months, at least 22 months, at least 23 months, at least two years, or more). This "low dose" device can be used in RP and/or macular telangiectasia patients.

In other embodiments, any of the devices described herein can secrete between 0.1 and 20 ng/day of CNTF upon implantation and between 0.6-5.0 ng/day (e.g., 0.6-2.8 ng/day) of CNTF following implantation for at least 12 months (e.g., at least 13 months, at least 14 months, at least 15 months, at least 16 months, at least 17 months, at least 18 months, at least 19 months, at least 20 months, at least 21 months, at least 22 months, at least 23 months, at least two years, or more). This "high dose" device can be used in glaucoma patients.

Any of these devices can also include a tether anchor, for example an anchor loop that is adapted for anchoring the device to an ocular structure.

In any of the devices described herein, the semi-permeable membrane is a permselective, immunoprotective membrane. Additionally (or alternatively), the semi-permeable membrane is an ultrafiltration membrane or a microfiltration membrane. In embodiments, the semi-permeable membrane has a median pore size of 100 nm. The semi-permeable membrane may also be made from a non-porous membrane material (e.g., a hydrogel or a polyurethane).

The nominal molecular weight cut off (MWCO) of the semi-permeable membrane is 500 kD. The semi-permeable membrane is between 90-120 µm thick.

In embodiments, the length of the device is between 4 mm-11 mm. The devices described herein can have an internal diameter of between 0.9 mm-1.2 mm.

The devices described herein can be sealed using any method known in the art (e.g., using methyl methacrylate).

At least one additional biologically active molecule is co-delivered from the device. Those skilled in the art will recognize that the at least one additional biologically active molecule is from a non-cellular source or from a cellular source. For example, the at least one additional biologically active molecule is produced by one or more genetically engineered ARPE-19 cells in the core.

Any of the devices described herein may include two or more additional characteristics (e.g., 3, 4, 5, 6, 7, or all) selected from the group consisting of:
 a. the core comprises between $0.5$-$1.0 \times 10^6$ ARPE-19 cells;
 b. length of the device is between 4 mm-11 mm;
 c. the internal diameter of the device is between 0.9 mm-1.2 mm;
 d. the ends of the device are sealed using methyl methacrylate;
 e. the semi-permeable membrane has a median pore size of about 100 nm;
 f. the nominal molecular weight cut off (MWCO) of the semi-permeable membrane is 500 KD;
 g. the semi-permeable membrane is between 90-120 µm thick;
 h. core comprises an internal scaffold, wherein the scaffold comprises polyethylene terephthalate (PET) fibers that comprises between 40-85% of internal volume of the device; and
 i. combinations thereof.

Also provided are methods for making the ophthalmic biocompatible devices described herein by a) genetically engineering at least one ARPE-19 cell to secrete a cytokine, and b) encapsulating said genetically engineered ARPE-19 cell within a semipermeable membrane, wherein said membrane allows the diffusion of the cytokine therethrough.

BRIEF DESCRIPTION OF THE DRAWINGS

FIG. 1A is a graph that depicts the visual acuity one year following implant of the ophthalmic encapsulated cell therapy (ECT) device in patients who were either implanted with a low concentration CNTF secreting ECT device (Low=5±0.8 ng/day at implant), or a high concentration secreting ECT device (High=20±3.0 ng/day at implant). Sham patients did not receive a CNTF secreting ECT device. FIG. 1B is a graph that depicts the visual acuity of patients 72 months post-implant of the ophthalmic ECT device. FIG. 1C is a graph that depicts the visual acuity 72 months post-implant of the ophthalmic device in a group of 7 RP patients who received the ophthalmic ECT device in one eye only and received no treatment in the other eye. The y-axis of the graph represents the number of letters lost one year post implant of the device compared to the number of letters discernable by the patient at the time of implant.

FIG. 2 is a graph that depicts change in macular volume one year post-implant of the device in RP patients who received a CNTF-secreting ophthalmic ECT device. The RP patients enrolled in this study were scheduled to have the CNTF-secreting ophthalmic device implanted for 2 years. The y-axis represents change in macular volume in mm$^3$. The x-axis represents the treatment condition (implant vs. sham) and the dosage condition (low or high).

FIG. 3A is a graph that depicts the retinal thickness (in microns) one year post implant in RP patients who received either a low dose CNTF-secreting ophthalmic ECT device (5±0.8 ng/day at implant) or a high dose CNTF-secreting ophthalmic ECT device (20±3.0 ng/day at implant). FIG. 3B is a graph that depicts the outer nuclear layer (ONL) thickness (in microns) one year post-implant in the retina of RP patients who received either a low dose CNTF-secreting ophthalmic ECT device (5±0.8 ng/day at implant) or a high dose CNTF-secreting ophthalmic ECT device (20±3.0 ng/day at implant). FIG. 3C is a graph that depicts the ellipsoid zone (EZ) width of the retina (in degrees) 72 months post-transplant of the ophthalmic ECT device in a cohort of patients that participated in either a 12 month or a 24 month device implant study. FIG. 3D is a graph that depicts the ellipsoid zone (EZ) width of the retina (in degrees) in specific RP patients who received the CNTF-secreting ECT device in one eye, and no treatment in the other eye.

FIG. 18 is a series of graphs that depict the thickness in the nerve fiber layer in glaucoma patients that received a high dose CNTF-secreting ophthalmic ECT device (20±3.0 ng/day at implant) in one eye (lower graph) and received no treatment or a sham treatment in the other eye (fellow eye) (upper graph). The y-axis depicts thickness in microns, and the x-axis depicts the assay time point and cohort identity.

DETAILED DESCRIPTION OF THE INVENTION

Figure 1A:
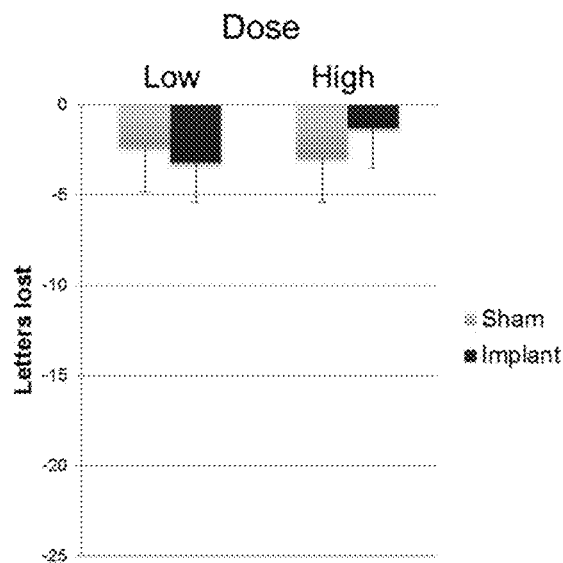
FIGS. 1A, 1B and 1C are a series of graphs that depict the visual acuity of retinitis pigmentosa (RP) patients one year following the implant of a CNTF-secreting ophthalmic cell culture device pre-loaded with ARPE-19 genetically engineered cells. This group of RP patients had the device implanted for one year.

Proteins are a dominant class of therapeutics used in the treatment of eye diseases. It has previously been demonstrated encapsulated cell technology (ECT) intraocular devices can deliver a biotherapeutic directly to the eye consistently for up to two years in human clinical trials. (See Kauper et al. 2012. *Invest Ophthalmol. Vis. Sci.* 53(12): 7484-91).

The devices and methods presented herein are useful for long-term stable expression of a wide range of biologically active molecules, including high molecular weight products up to 200 kD, to an individual in need of them. Biologically active molecules used in these devices and methods include a wide variety of factors normally secreted by various organs or tissues. By way of non-limiting example, biologically active molecules may include CNTF, BDNF, TGF-β, GDNF, NGF, bFGF, aFGF, IL-1β, IL-10, IFN-β, IFN-α, erythropoietin, growth hormone, Substance-P, neurotensin, NGF, NT-3, NT-4/5, GDNF, CDF/LIF, EGF, IGF, PDGF, bFGF, aFGF, P1GF, VEGF, VEGF-B, VEGF-C, and VEGF-D.

Another family of products suited to delivery using ECT devices includes biological response modifiers, including lymphokines and cytokines. Thus, these devices and methods are also useful for long-term, stable expression of biologically active molecules including hemoglobin, tyrosine hydroxylase, prohormone convertase, bcl-2, dopa decarboxylase, and dopamine beta-hydroxylase.

The biologically active molecules include molecules that are secreted from the capsule, or from an otherwise transplanted cell, and either directly or indirectly result in a biological effect in the mammalian host, as well as those biologically active molecules that directly or indirectly result in a biological effect on cells contained within the capsule. By way of non-limiting example, the genes encoding biologically active molecules include genes encoding CNTF, BDNF, TGF-β, GDNF, NGF, bFGF, aFGF, IL-1β, IL-10, IFN-β, IFN-α, erythropoietin, growth hormone, Substance-P, neurotensin, NGF, NT-3, NT-4/5, GDNF, CDF/LIF, EGF, IGF, PDGF, bFGF, aFGF, P1GF, VEGF, VEGF-B, VEGF-C, and VEGF-D.

Cultured clonal cell lines secrete all classes of biologically active molecules many on par with CHO-cell line based manufacturing systems. Clonal cell lines can exhibit robust recombinant protein secretion, with levels of some cell lines approaching 200-20,000 ng/million cells/day (20 pcd). In some embodiments, an iterative transfection process of one, two, three or more transfections can be used to genetically engineer the cells. Surprisingly, an iterative DNA transfection and selection significantly increases the ability of cell lines to produce recombinant protein secretion from 50,000 to greater than 70,000 ng/million cells/day (70 pcd). The iterative transfection process can be used to introduce multiple copies of the same or different biologically active molecules into the cells (e.g., ARPE-19 cells). Molecules produced with an iterative transfection process involving one transfection can be referred to as "first generation" molecules. Molecules produced with an iterative transfection process involving two transfections can be referred to as "second generation" molecules. Molecules produced with an iterative transfection process involving three transfections can be referred to as "third generation" molecules.

For example, cell lines producing active antibody scaffold based biologics have been successfully encapsulated and initial production of recombinant proteins from individual ECT devices were initially detected at levels up to 50-1000 ng/day. Subsequent iterative DNA transfected cell lines, in association with media optimization, increased ophthalmic ECT device levels up to 4,000 to 10,000 ng/day. (See WO 2012/075184, which is herein incorporated by reference).

Thus, ECT devices may be an effective drug delivery platform for large biologic molecules including antibodies, antibody scaffolds, and/or receptor fusion proteins for ophthalmic indications, as well as localized and/or systemic indications.

Ciliary neurotrophic factor (CNTF) is a protein that is involved in promoting neurotransmitter synthesis and neurite outgrowth in neuronal populations. CNTF is a survival factor for neuronal cells, including neurons and oligodendrocytes, and has been demonstrated to have a protective role for photoreceptors. This protective role for photoreceptors includes the promotion of cone outer segment regeneration (Li et al. *PLoS One*, 2010; 5(3)). Moreover, CNTF is also believed to play a role in the reduction of tissue destruction associated with inflammatory diseases.

Recent data suggests that human fetal retinal epithelial cells (hfRPE) produce CNTF and also express its receptors (Li et al. *PLoS One*, 2011; 6(9)). There is also evidence that, in addition to the role that CNTF has in the promoting survival and outgrowth of neurons, CNTF has a positive impact on the survival of retinal epithelial cells. (Id.). Collectively, the evidence indicates that CNTF levels may play a role in the regulation of neuronal cell viability as well as in the regulation of steady-state neuronal homeostasis.

Vascular endothelial growth factor (VEGF) is a signaling protein involved in both vasculogenesis, the formation of the embryonic circulatory system, and angiogenesis, the growth of blood vessels from pre-existing vasculature. While VEGF is mostly known for its effects on cells of the vascular endothelium, it also affects a broad range of other cells types, e.g., stimulation monocyte/macrophage migration, neurons, cancer cells, kidney epithelial cells, etc.

There are a number of proteins within the VEGF family, which arise as a result of alternate splicing of mRNA. The various splice variants impact the function of VEGF, as they determine whether the resulting proteins are pro- or anti-angiogenic. Additionally, the splice variants also effect the interaction of VEGF with heparin sulfate proteoglycans (HSPGs) and neuripilin co-receptors on the cell surface, which, in turn, enhances the ability of VEGF to bind to and activate VEGF signaling receptors (VEGFRs).

The VEGF splice variants are released from cells as glycosylated disulfide-bonded dimers. Structurally, VEGF belongs to the PDGF family of cysteine-knot growth factors, and, thus, several closely-related proteins exist, i.e., placenta growth factor (P1GF), VEGF-B, VEGF-C and VEGF-D, which together comprise the VEGF sub-family of growth factors. VEGF itself is commonly referred to as VEGF-A in order to differentiate it from these other, related growth factors.

The VEGF family of proteins stimulates cellular response by binding to the VEGFRs or to the tyrosine kinase receptors present on a cell surface. VEGF receptors have an extracellular portion consisting of seven immunoglobulin-like domains, a single transmembrane spanning region, and an intracellular portion containing a split tyrosine-kinase domain. VEGF-A binds to both VEGFR-1 (Flt-1) and VEGFR-2 (KDR/Flk-1). VEGFR1 is expressed as a full-length receptor tyrosine kinase (RTK) as well as in a soluble form, which carries only the extracellular domain. VEGFR-2 appears to mediate almost all of the known cellular responses to VEGF and is expressed in mesodermal progenitor cells that are destined to differentiate into hemangioblasts and angioblasts. The function of VEGFR-1 is less well-defined, although it is thought to modulate VEGFR-2 signaling. VEGF-C and VEGF-D, but not VEGF-A, are also ligands for a third receptor (VEGFR-3), which mediates lymphangiogenesis.

Platelet Derived Growth Factor (PDGF) is a growth factor that also plays a role in angiogenesis. Multiple forms of PDGF exists, composed dimers containing two A chains (AA), two B chains (BB), or a mixed A/B chain (AB). PDGF is a potent mitogen for pericytes, a class of cells that serve as support for endothelial cell growth. PDGF receptor (PDGFR) exists in two forms, alpha and beta. PDGFR beta has the highest affinity for PDGF-BB and has been shown to exert anti-angiogenic biological effect as a secreted protein in either fusion protein—Fc form or as an extracellular soluble receptor. Recently, potent synergistic anti-angiogenic activity has been demonstrated in mouse ocular vascular neogenesis models involving the combination of anti-VEGF molecules and antagonistic PDGF molecules. Thus a combination anti-PDGF, anti-VEGF therapy may exert a higher anti-angiogenic activity than anti-VEGF therapy alone.

Other examples of proteins of interest include, but are not limited to, BDNF, TGF-β, GDNF, NGF, bFGF, aFGF, IL-1β, IL-10, IFN-β, and IFN-α. Among these proteins, the following have been demonstrated to promote neuron survival: BDNF (Lipsky and Marini, 2007, *Ann NY Acad Sci*, 1122: 130-43), TGF-β (see Krieglstein et al *J. Physiol Paris*, 2002, 96(1-2):25-30), GDNF (see Suzuki et al. PLoS, 2007, 2(8): e689), NGF (Chun and Patterson, J C B, 1977 (75): 694-704), bFGF (see Meijs et al. *J Neurotrauma* 2004, 21(10): 1415-30), aFGF (Lipton et al. 1988, *PNAS* 85: 2388-2392), IL-10 (Boyd et al., *Invest. Ophthalmol. Vis. Sci.* 44:5206-5211), IFN-β (Sattler et al., *Exp Neurol*, 2006, 201(1): 172-81), and IFN-α (He Yang et al. PNAS, 2000, 97(25): 13631-13636).

A gene of interest (i.e., a gene that encodes a given biologically active molecule) can be inserted into a cloning site of a suitable expression vector using standard techniques known in the art. The nucleic acid and amino acid sequences of the human (and other mammalian) genes encoding suitable biologically active molecules are known. For example, the sequences of CNTF can be found at GenBank Accession X60477.1. See, e.g., U.S. Pat. Nos. 4,997,929; 5,141,856; 5,364,769; 5,453,361; WO 93/06116; WO 95/30686, incorporated herein by reference.

In some embodiments, the same molecule can be introduced into different expression vectors, thereby making different plasmids. Using the iterative transfection process described herein, multiple copies of the same (or different) biologically active molecules can be incorporated into a cell (e.g., an ARPE-19 cell).

Any method(s) for genetically engineering cells (i.e., ARPE-19 cells) known in the art can be used to create cell lines that produce therapeutically effective amounts of biologically active molecules, such as, for example, CNTF.

As used herein, the term "therapeutically effective amounts" and the like, describes an amount of a biologically active molecule that has a beneficial or therapeutic clinical outcome when administered to a subject.

A wide variety of host/expression vector combinations may be used to express the gene encoding the growth factor, or other biologically active molecule(s) of interest. Long-term, stable in vivo expression is achieved using expression vectors (i.e., recombinant DNA molecules) in which the gene encoding the biologically active molecule is operatively linked to a promoter that is not subject to down regulation upon implantation in vivo in a mammalian host. Suitable promoters include, for example, strong constitutive mammalian promoters, such as beta-actin, eIF4A1, GAPDH, etc. Stress-inducible promoters, such as the met-allothionein 1 (MT-1) or VEGF promoter may also be suitable. Additionally, hybrid promoters containing a core promoter and custom 5' UTR or enhancer elements may be used. Other known non-retroviral promoters capable of controlling gene expression, such as CMV or the early and late promoters of SV40 or adenovirus are suitable. Enhancer elements may also be utilized to confer additional gene expression under stress environments, such as low $O_2$. One example is the erythropoietin enhancer which confers up-regulation of associated gene elements upon hypoxic induction.

The expression vectors containing the gene of interest may then be used to transfect the desired cell line. Standard transfection techniques such as liposomal, calcium phosphate co-precipitation, DEAE-dextran transfection or electroporation may be utilized. Commercially available mammalian transfection kits, such as Fugene6 (Roche Applied Sciences), may be purchased. Additionally, viral vectors may be used to transduce the desired cell line. An example of a suitable viral vector is the commercially available pLenti family of viral vectors (Invitrogen). Human or mammalian cells can be used. In all cases, it is important that the cells or tissue contained in the device are not contaminated or adulterated.

For antibody scaffold proteins requiring heavy and light chain components, dual constructs, each encoding a relevant antibody heavy or light chain, can be co-transfected simultaneously, thereby yielding cell lines expressing functional bivalent Fab and tetravalent full antibody molecules.

Preferred promoters used in the disclosed constructs include the SV40 promoter and the CMV/EF1alpha promoter. (See U.S. Pat. No. 5,639,275).

Other useful expression vectors, for example, may contain segments of chromosomal, non-chromosomal and synthetic DNA sequences, such as various known derivatives of SV40 and known bacterial plasmids, e.g., pUC, pBlueScript™ plasmids from E. coli including pBR322, pCR1, pMB9 and their derivatives. Expression vectors containing the geneticin (G418), hygromycin or blasticidin drug selection genes (Southern, P. J., In Vitro, 18, p. 315 (1981), Southern, P. J. and Berg, P., J. Mol. Appl. Genet., 1, p. 327 (1982)) are also useful. These vectors can employ a variety of different enhancer/promoter regions to drive the expression of both a biologic gene of interest and/or a gene conferring resistance to selection with toxin such as G418, hygromycin B, or blasticidin. A variety of different mammalian promoters can be employed to direct the expression of the genes for G418 and hygromycin B and/or the biologic gene of interest. The G418 resistance gene codes for aminoglycoside phosphotransferase (APH) which enzymatically inactivates G418 (100-1000 µg/µl) added to the culture medium. Only those cells expressing the APH gene will survive drug selection usually resulting in the expression of the second biologic gene as well. The hygromycin B phosphotransferase (HPH) gene codes for an enzyme which specifically modifies hygromycin toxin and inactivates it. Genes co-transfected with or contained on the same plasmid as the hygromycin B phosphotransferase gene will be preferentially expressed in the presence of hygromycin B at 50-200 µg/ml concentrations.

Examples of expression vectors that can be employed include, but are not limited to, the commercially available pRC/CMV (Invitrogen), pRC/RSV (Invitrogen), pCDNA1NEO (Invitrogen), pCI-Neo (Promega), pcDNA3.3 (Invitrogen) and GS vector system (Lonza Group, Switzerland). Other suitable commercially available vectors include pBlast, pMono, or pVitro. In one preferred embodiment, the expression vector system is the pCpGfree-vitro expression vectors available with neomycin (G418), hygromycin, and blasticidin resistance genes (InvivoGen, San Diego, Calif.)).

In one embodiment, the pNUT expression vector, which contains the cDNA of the mutant DHFR and the entire pUC18 sequence including the polylinker, can be used. See, e.g., Aebischer, P., et al., Transplantation, 58, pp. 1275-1277 (1994); Baetge et al., PNAS, 83, pp. 5454-58 (1986). The pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above.

Those skilled in the art will recognize that any other suitable, commercially available expression vectors (e.g., pcDNA family (Invitrogen), pBlast, pMono, pVitro, or pCpG-vitro (Invivogen)) can also be used. Principal elements regulating expression are typically found in the expression cassette. These elements include the promoter, 5' untranslated region (5' UTR) and 3' untranslated region (3' UTR). Other elements of a suitable expression vector may be critical to plasmid integration or expression but may not be readily apparent. The skilled artisan will be able to design and construct suitable expression vectors for use. The choice, design, and/or construction of a suitable vector are well within the routine level of skill in the art.

The genes and cDNA encoding the VEGF1, VEGF2, PDGF alpha, and PDGF beta receptors have been cloned and their nucleotide sequences published. (GenBank Accession U01134 and AF063658, NM_006206, BC032224). Likewise, the nucleotide and amino acid sequences of CNTF have also been published. (GenBank Accession X60477.1 and P26441.1). Other genes encoding biologically active molecules that are not publicly available may be obtained using standard recombinant DNA methods such as PCR amplification, genomic and cDNA library screening with oligonucleotide probes. Any of the known genes coding for biologically active molecules may be employed in any of the methods described herein.

The cell of choice is the ARPE-19 cell line, a spontaneously arising continuous human retinal pigmented epithelial cell line. However, those skilled in the art will recognize that other suitable cells, including by not limited to CHO cells, BHK cells, RPE (primary cells or immortalized cells), can also be used. The choice of cell depends upon the intended application. The encapsulated cells may be chosen for secretion of a particular biologically active molecule construct. Cells can also be employed which synthesize and secrete agonists, analogs, derivatives or fragments of the construct, which are active. Those skilled in the art will recognize that other suitable cell types may also be genetically engineered to secrete any of the biologically active molecules described herein.

To be a platform cell line for an encapsulated cell based delivery system, the cell line should have as many of the following characteristics as possible: (1) the cells should be hardy under stringent conditions (the encapsulated cells should be functional in the avascular tissue cavities such as in the central nervous system or the eye, especially in the intra-ocular environment); (2) the cells should be able to be genetically modified (the desired therapeutic factors needed to be engineered into the cells); (3) the cells should have a relatively long life span (the cells should produce sufficient progenies to be banked, characterized, engineered, safety tested and clinical lot manufactured); (4) the cells should preferably be of human origin (which increases compatibility between the encapsulated cells and the host); (5) the cells should exhibit greater than 80% viability for a period of more than one month in vivo in device (which ensures long-term delivery); (6) the encapsulated cells should deliver an efficacious quantity of a useful biological product (which ensures effectiveness of the treatment); (7) the cells should have a low level of host immune reaction (which ensures the longevity of the graft); and (8) the cells should be nontumorigenic (to provide added safety to the host, in case of device leakage).

The ARPE-19 cell line (see Dunn et al., 62 Exp. Eye Res. 155-69 (1996), Dunn et al., 39 Invest. Ophthalmol. Vis. Sci. 2744-9 (1998), Finnemann et al., 94 Proc. Natl. Acad. Sci. USA 12932-7 (1997), Handa et al., 66 Exp. Eye. 411-9 (1998), Holtkamp et al., 112 Clin. Exp. Immunol. 34-43 (1998), Maidji et al., 70 J. Virol. 8402-10 (1996); U.S. Pat. No. 6,361,771) demonstrates all of the characteristics of a successful platform cell for an encapsulated cell-based delivery system. The ARPE-19 cell line is available from the American Type Culture Collection (ATCC Number CRL-2302). ARPE-19 cells are normal retinal pigmented epithelial (RPE) cells and express the retinal pigmentary epithelial cell-specific markers CRALBP and RPE-65. ARPE-19 cells form stable monolayers, which exhibit morphological and functional polarity.

Genetically engineered ARPE-19 cells express one or more biologically active molecules to produce a therapeutic amount of the biologically active molecule. In some embodiments, the genetically engineered ARPE-19 cells are capable of producing at least 10,000 ng/day/$10^6$ cells. Preferably, these cells are capable of producing this amount for a period of at least 3 months. (e.g. at least 3, 4, 5, 6, 7, 8, 9, 10, 11, 12, 13, 14, 15, 16, 17, 18, 19, 20, 21, 22, 23, or 24 months or more).

0.5 to $1.0 \times 10^6$ ARPE-19 cells that have been genetically engineered to secrete biologically active molecules can be loaded into the ECT device to produce appropriate dosage levels for the condition to be treated. For example, 0.5 to $1.0 \times 10^6$ ARPE-19 cells genetically engineered to secrete CNTF can be used as the cellular source for the ECT device for the treatment of RP, glaucoma, geographic atrophy, and macular telangiectasia. For the treatment of RP and macular telangiectasia the devices secrete between 0.1 and 20 ng/CNTF/day (e.g. 0.1, 0.2, 0.3, 0.4, 0.5, 0.6, 0.7. 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, or 20.0 ng/CNTF/day) at the time of implantation of the device, and between 0.1 and 0.4 ng/CNTF/day (e.g. 0.1, 0.2, 0.3, 0.4 ng/CNTF/day) at least two years after initial implantation. Appropriate dosage amounts of CNTF for the treatment of glaucoma and geographic atrophy is between 0.1 and 20 ng/CNTF/day (e.g. 0.1, 0.2, 0.3, 0.4, 0.5, 0.6, 0.7. 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, or 20.0 ng/CNTF/day) at the time of implantation of the device, and between 0.6 and 5.0 ng/CNTF/day (e.g. 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 ng/CNTF/day) two years after initial implantation.

When the devices are used, preferably between $10^2$ and $10^8$ engineered ARPE-19 cells, most preferably 0.5-$1.0 \times 10^6$ or $5 \times 10^2$ to $6 \times 10^5$ ARPE-19 cells that have been genetically engineered to secrete one or more biologically active molecules described herein are encapsulated in each device. Dosage may be controlled by implanting a fewer or greater number of capsules, preferably between 1 and 50 capsules per patient. The ophthalmic ECT devices described herein are capable of delivering between about 0.1 pg and 1000 µg of the biologically active molecules per eye per patient per day. In one non-limiting example, the therapeutic amount is 500-50,000 ng steady state per eye. In another example, the therapeutic amount is at least 10 µg/ml steady state per eye. Moreover, the cells lines and devices are able to express this therapeutic amount for a period of at least three months. (e.g. at least 3, 4, 5, 6, 7, 8, 9, 10, 11, 12, 13, 14, 15, 16, 17, 18, 19, 20, 21, 22, 24 or more months).

Techniques and procedures for isolating cells or tissues which produce a selected product are known to those skilled in the art, or can be adapted from known procedures with no more than routine experimentation.

If the cells to be isolated are replicating cells or cell lines adapted to growth in vitro, it is particularly advantageous to generate a cell bank of these cells. A particular advantage of a cell bank is that it is a source of cells prepared from the same culture or batch of cells. That is, all cells originated from the same source of cells and have been exposed to the same conditions and stresses. Therefore, the vials can be treated as homogenous culture. In the transplantation context, this greatly facilitates the production of identical or replacement devices. It also allows simplified testing protocols, which insure that implanted cells are free of retroviruses and the like. It may also allow for parallel monitoring of vehicles in vivo and in vitro, thus allowing investigation of effects or factors unique to residence in vivo.

As used herein, the terms "individual" or "recipient" or "host" and the like are used interchangeably to refer to a human or an animal subject.

A "biologically active molecule" ("BAM") is a substance that is capable of exerting a biologically useful effect upon the body of an individual in whom a device is implanted. In one embodiment, the BAM is CNTF. For example, the neuronal survival cytokines described herein are examples of BAMs. Other examples of BAMs include, TGF-β, NGF, IL-1β, IL-10, IFN-β, IFN-α, erythropoietin, growth hormone, Substance-P, neurotensin, NGF, BDNF, NT-3, NT-4/5, GDNF, CDF/LIF, EGF, IGF, PDGF, bFGF, aFGF, P1GF, VEGF, VEGF-B, VEGF-C, and VEGF-D.

The terms "capsule" and "device" and "vehicle" and the like are used interchangeably herein to refer to the ECT devices.

Unless otherwise specified, the term "cells" means cells in any form, including but not limited to cells retained in tissue, cell clusters, and individually isolated cells.

As used herein a "biocompatible capsule" or "biocompatible device" or "biocompatible vehicle" means that the capsule or device or vehicle, upon implantation in an individual, does not elicit a detrimental host response sufficient to result in the rejection of the capsule or to render it inoperable, for example through degradation.

As used herein an "immunoisolatory capsule" or "immunoprotective capsule" or "immunoisolatory device" or "immunoprotective device" or "immunoisolatory vehicle" or "immunoprotective vehicle" means that the capsule upon implantation into an individual, favorably partitions the device cellular contents and minimizes the deleterious effects of the host's immune system on the cells within its core.

As used herein "long-term, stable expression of a biologically active molecule" means the continued production of a biologically active molecule at a level sufficient to maintain its useful biological activity for periods greater than one month, preferably greater than three months and most preferably greater than six months. Implants of the devices and the contents thereof are able to retain functionality for greater than three months in vivo and, in many cases, for longer than two years or more.

The terms "jacket" and "semi-permeable membrane" and the like are used interchangeably herein.

The term "internal scaffold" is one example of a "matrix" that can be used in the devices described herein.

The "semi-permeable" nature of the jacket membrane surrounding the core permits molecules produced by the cells (e.g., metabolites, nutrients and/or therapeutic substances) to diffuse from the device into the surrounding host eye tissue, but is sufficiently impermeable to protect the cells in the core from detrimental immunological attack by the host.

The exclusion of IgG from the core of the vehicle is not the touchstone of immunoisolation, because in most cases IgG alone is insufficient to produce cytolysis of the target cells or tissues. Thus, for immunoisolatory capsules, jacket nominal molecular weight cutoff (MWCO) values up to 1000 kD are contemplated. Preferably, the MWCO is between 50-700 kD. Most preferably, the MWCO is between 70-300 kD. See, e.g., WO 92/19195. In one preferred embodiment, the MWCO is 500 kD.

Described herein are biocompatible, optionally immunoisolatory and/or immunoprotective devices for the delivery of one or more of the biologically active molecules described herein to the eye. Such devices contain a core containing living cells that produce or secrete the biologically active molecules and a biocompatible jacket surrounding the core, wherein the jacket has a molecular weight cut off ("MWCO") that allows the diffusion of the biologically active molecule into the eye.

Described herein are biocompatible and implantable and optionally immunoisolatory and/or immunoprotective devices, containing a core having cells that produces or secretes one or more biologically active molecules and a semi-permeable membrane surrounding the cells, which permits the diffusion of the one or more biologically active molecules there through.

A variety of biocompatible capsules are suitable for delivery of molecules. Useful biocompatible polymer capsules comprise (a) a core which contains a cell or cells, either suspended in a liquid medium or immobilized within a biocompatible matrix, and (b) a surrounding jacket comprising a membrane which does not contain isolated cells, which is biocompatible, and permits diffusion of the cell-produced biologically active molecule into the eye.

Many transformed cells or cell lines are advantageously isolated within a capsule having a liquid core, comprising, e.g., a nutrient medium, and optionally containing a source of additional factors to sustain cell viability and function. The core of the devices can function as a reservoir for growth factors (e.g., prolactin, or insulin-like growth factor 2), growth regulatory substances such as transforming growth factor β (TGF-β) or the retinoblastoma gene protein or nutrient-transport enhancers (e.g., perfluorocarbons, which can enhance the concentration of dissolved oxygen in the core). Certain of these substances are also appropriate for inclusion in liquid media.

In addition, any of the devices described herein can also be used as a reservoir for the controlled delivery of needed drugs or biotherapeutics. In such cases, the core contains a high concentration of the selected drug or biotherapeutic (alone or in combination with cells or tissues). In addition, satellite vehicles containing substances which prepare or create a hospitable environment in the area of the body in which a device is implanted can also be implanted into a recipient. In such instances, the devices containing immunoisolated cells are implanted in the region along with satellite vehicles releasing controlled amounts of, for example, a substance which down-modulates or inhibits an inflammatory response from the recipient (e.g., anti-inflammatory steroids), or a substance which stimulates the ingrowth of capillary beds (e.g., an angiogenic factor).

Alternatively, the core may comprise a biocompatible matrix of a hydrogel or other biocompatible material (e.g., extracellular matrix components) which stabilizes the position of the cells. The term "hydrogel" herein refers to a three dimensional network of cross-linked hydrophilic polymers. The network is in the form of a gel, substantially composed of water, preferably gels being greater than 90% water. Compositions which form hydrogels fall into three classes. The first class carries a net negative charge (e.g., alginate). The second class carries a net positive charge (e.g., collagen and laminin). Examples of commercially available extracellular matrix components include Matrigel™ and Vitrogen™. The third class is net neutral in charge (e.g., highly cross-linked polyethylene oxide, or polyvinylalcohol).

Any suitable matrix or spacer may be employed within the core, including precipitated chitosan, synthetic polymers and polymer blends, microcarriers and the like, depending upon the growth characteristics of the cells to be encapsulated.

Alternatively, the devices may have an internal scaffold. The scaffold may prevent cells from aggregating and improve cellular distribution within the device. (See PCT publication no. WO 96/02646). The scaffold defines the microenvironment for the encapsulated cells and keeps the cells well distributed within the core. The optimal internal scaffold for a particular device is highly dependent on the cell type to be used. In the absence of such a scaffold, adherent cells aggregate to form clusters.

For example, the internal scaffold may be a yarn or a mesh. The filaments used to form a yarn or mesh internal scaffold are formed of any suitable biocompatible, substantially non-degradable material. (See U.S. Pat. Nos. 6,303,136 and 6,627,422, which are herein incorporated by reference). Preferably, the capsule will be similar to those described by PCT International patent applications WO 92/19195 or WO 95/05452, incorporated by reference; or U.S. Pat. Nos. 5,639,275; 5,653,975; 4,892,538; 5,156,844; 5,283,187; or 5,550,050, incorporated by reference. Materials useful in forming yarns or woven meshes include any biocompatible polymers that are able to be formed into fibers such as, for example, acrylic, polyester, polyethylene, polypropylene, polyacrylonitrile, polyethylene terephthalate, nylon, polyamides, polyurethanes, polybutester, or natural fibers such as cotton, silk, chitin or carbon. Any suitable thermoplastic polymer, thermoplastic elastomer, or other synthetic or natural material having fiber-forming properties may be inserted into a pre-fabricated hollow fiber membrane or a hollow cylinder formed from a flat membrane sheet. For example, silk, PET or nylon filaments used for suture materials or in the manufacture of vascular grafts are highly conducive to this type of application. In other embodiments, metal ribbon or wire may be used and woven. Each of these filament materials has well-controlled surface and geometric properties, may be mass produced, and has a long history of implant use. In certain embodiments, the filaments may be "texturized" to provide rough surfaces and "hand-holds" onto which cell projections may attach. The filaments may be coated with extracellular matrix molecules or surface-treated (e.g. plasma irradiation) to enhance cellular adhesion to the filaments.

In some embodiments, the filaments, preferably organized in a non-random unidirectional orientation, are twisted in bundles to form yarns of varying thickness and void volume. Void volume is defined as the spaces existing between filaments. The void volume in the yarn should vary between 20-95%, but is preferably between 50-95%. In one preferred embodiment, the internal scaffold is made from PET fibers that fill between 40-85% of the internal volume of the devices. The preferred void space between the filaments is between 20-200 µm, sufficient to allow the scaffold to be seeded with cells along the length of the yarn, and to allow the cells to attach to the filaments. The preferred diameter of the filaments comprising the yarn is between 5-100 µm. These filaments should have sufficient mechanical strength to allow twisting into a bundle to comprise a yarn. The filament cross-sectional shape can vary, with circular, rectangular, elliptical, triangular, and star-shaped cross-section being preferred.

Alternatively, the filaments or yarns can be woven into a mesh. The mesh can be produced on a braider using carriers, similar to bobbins, containing monofilaments or multifilaments, which serve to feed either the yarn or filaments into the mesh during weaving. The number of carriers is adjustable and may be wound with the same filaments or a combination of filaments with different compositions and structures. The angle of the braid, defined by the pick count, is controlled by the rotational speed of the carriers and the production speed. In one embodiment, a mandrel is used to produce a hollow tube of mesh. In certain embodiments, the braid is constructed as a single layer, in other embodiments it is a multi-layered structure. The tensile strength of the braid is the linear summation of the tensile strengths of the individual filaments.

In other embodiments, a tubular braid is constructed. The braid can be inserted into a hollow fiber membrane upon which the cells are seeded. Alternatively, the cells can be allowed to infiltrate the wall of the mesh tube to maximize the surface area available for cell attachment. When such cell infiltration occurs, the braid serves both as a cell scaffold matrix and as an inner support for the device. The increase in tensile strength for the braid-supported device is significantly higher than in alternative approaches.

As noted, for implant sites that are not immunologically privileged, such as periocular sites, and other areas outside the anterior chamber (aqueous) and the posterior chamber (vitreous), the capsules are preferably immunoisolatory. Components of the biocompatible material may include a surrounding semipermeable membrane and the internal cell-supporting scaffolding. The transformed cells are preferably seeded onto the scaffolding, which is encapsulated by the permselective membrane, which is described above. Also, bonded fiber structures can be used for cell implantation. (See U.S. Pat. No. 5,512,600, incorporated by reference). Biodegradable polymers include, for example, those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (PCT International patent application Ser. No. 98/05304, incorporated by reference). Woven mesh tubes have been used as vascular grafts (PCT International patent application WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fiber membrane. Such membranes and methods of making them are disclosed by U.S. Pat. Nos. 5,284,761 and 5,158,881, incorporated by reference. The surrounding semipermeable membrane is formed from a polyether sulfone hollow fiber, such as those described by U.S. Pat. Nos. 4,976,859 or 4,968,733, incorporated by reference. An alternate surrounding semipermeable membrane material is polysulfone.

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired.

Preferably the device has a tether that aids in maintaining device placement during implant, and aids in retrieval. Such a tether may have any suitable shape that is adapted to secure the capsule in place. For example, the suture may be a loop, a disk, or a suture. In some embodiments, the tether is shaped like an eyelet, so that suture may be used to secure the tether (and thus the device) to the sclera, or other suitable ocular structure. In another embodiment, the tether is continuous with the capsule at one end, and forms a pre-threaded suture needle at the other end. In one preferred embodiment, the tether is an anchor loop that is adapted for anchoring the capsule to an ocular structure. The tether may be constructed of a shape memory metal and/or any other suitable medical grade material known in the art.

In a hollow fiber configuration, the fiber will have an inside diameter of less than 2000 microns, preferably less than 1200 microns. Also contemplated are devices having an outside diameter less than 300-600 microns. In one preferred embodiment, the inner diameter is between 0.9 mm and 1.2 mm. For implantation in the eye, in a hollow fiber configuration the capsule will preferably be between 0.4 cm to 1.5 cm in length, most preferably between 0.4 to 1.0 cm in length. In one preferred embodiment, the length of the device is between 4 mm and 11 mm. Longer devices may be accommodated in the eye, however, a curved or arcuate shape may be required for secure and appropriate placement. The hollow fiber configuration is preferred for intraocular placement.

For periocular placement, either a hollow fiber configuration (with dimensions substantially as above) or a flat sheet configuration is contemplated. The upper limit contemplated for a flat sheet is approximately 5 mm×5 mm—assuming a square shape. Other shapes with approximately the same surface area are also contemplated.

Microdevices manufactured for delivery of the biologically active molecule may have a length of between 1 and 2.5 millimeters, with an inner diameter of between 300 and 500 microns and an outer diameter of between 450 and 700 microns. In such micronized devices, an inner scaffolding containing between 10 and 60 monofilaments of PET can be utilized. The molecular weight cut off ranges from these micronized devices are between 100 and 2000 kDa. In contrast, passive diffusion of a 70 kDa dextran ranges between 100 and 2000×10$^{-10}$ cm$^2$/s. While any suitable membrane material(s) described herein may be used in these micronized devices, two preferred materials are polyethersulfone and/or polysulfone. Moreover, microdevices can be manufactured with and without anchors made of a suitable material (e.g., nitinol). For a complete discussion of micronized devices, see WO2007/078922, which is herein incorporated by reference.

The permselective feature of the membrane contemplated for use in the delivery of biologically active molecules described herein has been manufactured by the phase inversion process, know to those familiar with the art, to reside within the inner skin of the membrane. Development of the permselective feature of rejecting skin on the inner surface improves the manufacturing consistency of the pore structure and control of the rejection properties while also protecting the membrane properties throughout the downstream manufacture of the encapsulating device. The permselective feature of the membrane described is developed to allow passage of molecular sizes required for therapeutic necessity; however, the characteristics have also been optimized to allow the largest size necessary to be released while restricting molecules only slightly larger than the intended protein size from entering the capsule.

Due to the allogenic nature of interaction between the cells used and the host recipient, the greatest concern to rejection is from the host immune cell complex mediated attack directly against the transplanted, encapsulated cells rather than from a cytolytic complement mediated attack complex or by interaction of antibody interaction with complement. While the membranes used described herein are designed to allow passage of molecules up to the size of immunoglobulin G the membrane will still restrict transport of molecules such as Clq (about 400 kDa), the largest molecule required for the assembly of the cellular attack complex. The design of the membrane described herein, therefore, will maximize the nutrient and metabolite exchange rate with the host, supporting long-term viability of the transplanted cells within the host, allowing for substantial delivery of the target therapeutic molecules from the encapsulated cells to the host, while preventing complement recognition of the encapsulated cells and direct cell contact with the host.

The open membrane contemplated for use with the biologically active molecules described herein will have nominal molecular weight cutoff (MWCO) values up to 1000 kD. Preferably, the MWCO is between 50-700 kD and ideally approximately 300 kD. In one preferred embodiment, the MWCO is 500 kD. The nominal pore size of the membrane contemplated will have a nominal pore size of approximately 100 nm and based upon a Gaussian distribution of pores the largest absolute pores would be less than 150 nm. The passive diffusion of a dextran molecule of the size 70 kDa is between 100 and 2000×10$^{-10}$ cm$^2$/s, and preferably the diffusion coefficient of a 70 kDa dextran is closer to 2000×10$^{-10}$ cm$^2$/s. The open membrane used with biologically active molecules will have an upper hydraulic permeability value of approximately 100 mls/min/m$^2$/mmHg. Alternatively, if a very open membrane is not utilized, a more "immunoisolatory" and/or "immunoprotective" membrane will be used. For such an immunoisolatory membrane, the hydraulic permeability will typically be in the range of 0.4-170 mls/min/m$^2$/mmHg, for example, 0.5-100 mls/min/m$^2$/mmHg, preferably in the range of 15 to 50 mls/min/m$^2$/mmHg. Using the testing procedures to determine a single molecular weight rejection recognized by those familiar with the art, the nominal molecular weight cutoff of a more "immunoisolatory" membrane will reject 90% of bovine albumin while the diffusive flux of a 70 kDa dextran molecule will remain approximately 2000×10$^{-10}$ cm$^2$/s. The glucose mass transfer coefficient of the capsule, defined, measured and calculated as described by Dionne et al., ASAIO Abstracts, p. 99 (1993), and Colton et al., The Kidney, eds., Brenner B M and Rector F C, pp. 2425-89 (1981) will be greater than 10$^{-6}$ cm/sec, preferably greater than 10$^{-4}$ cm/sec.

In one preferred embodiment, the median pore size is about 100 nm. The surrounding or peripheral region (jacket), which surrounds the core of the devices can be permselective, biocompatible, and/or immunoisolatory. It is produced in such a manner that it is free of isolated cells, and completely surrounds (i.e., isolates) the core, thereby preventing contact between any cells in the core and the recipient's body. Biocompatible semi-permeable hollow fiber membranes, and methods of making them are disclosed in U.S. Pat. Nos. 5,284,761 and 5,158,881 (See also, WO 95/05452), each of which incorporated herein by reference in its entirety. For example, the capsule jacket can be formed from a polyether sulfone hollow fiber, such as those described in U.S. Pat. Nos. 4,976,859 and 4,968,733, and 5,762,798, each incorporated herein by reference.

To be permselective, the jacket is formed in such a manner that it has a molecular weight cut off ("MWCO") range appropriate both to the type and extent of immunological reaction anticipated to be encountered after the device is implanted and to the molecular size of the largest substance whose passage into and out of the device into the eye is desirable. The type and extent of immunological attacks which may be mounted by the recipient following implantation of the device depend in part upon the type(s) of moiety isolated within it and in part upon the identity of the recipient (i.e., how closely the recipient is genetically related to the source of the BAM). When the implanted tissue or cells are allogeneic to the recipient, immunological rejection may proceed largely through cell-mediated attack by the recipient's immune cells against the implanted cells. When the tissue or cells are xenogeneic to the recipient, molecular attack through assembly of the recipient's cytolytic complement attack complex may predominate, as well as the antibody interaction with complement.

The jacket allows passage of substances up to a predetermined size, but prevents the passage of larger substances. More specifically, the surrounding or peripheral region is produced in such a manner that it has pores or voids of a predetermined range of sizes, and, as a result, the device is permselective. The MWCO of the surrounding jacket must be sufficiently low to prevent access of the substances required to carry out immunological attacks to the core, yet sufficiently high to allow delivery of the biologically active molecules to the recipient. Preferably, when truncated biologically active molecules are used, the MWCO of the biocompatible jacket of the devices is from about 1 kD to about 150 kD. However, if delivery of a non-truncated biologically active molecules is desired, an open membrane with a MWCO greater than 200 kD should be used.

As used herein with respect to the jacket of the device, the term "biocompatible" refers collectively to both the device and its contents. Specifically, it refers to the capability of the implanted intact device and its contents to avoid the detrimental effects of the body's various protective systems and to remain functional for a significant period of time. As used herein, the term "protective systems" refers to the types of immunological attack which can be mounted by the immune system of an individual in whom the instant vehicle is implanted, and to other rejection mechanisms, such as the fibrotic response, foreign body response and other types of inflammatory response which can be induced by the presence of a foreign object in the individuals' body. In addition to the avoidance of protective responses from the immune system or foreign body fibrotic response, the term "biocompatible", as used herein, also implies that no specific undesirable cytotoxic or systemic effects are caused by the vehicle and its contents such as those that would interfere with the desired functioning of the vehicle or its contents.

The external surface of the device can be selected or designed in such a manner that it is particularly suitable for implantation at a selected site. For example, the external surface can be smooth, stippled or rough, depending on whether attachment by cells of the surrounding tissue is desirable. The shape or configuration can also be selected or designed to be particularly appropriate for the implantation site chosen.

The biocompatibility of the surrounding or peripheral region (jacket) of the device is produced by a combination of factors. Important for biocompatibility and continued functionality are device morphology, hydrophobicity and the absence of undesirable substances either on the surface of, or leachable from, the device itself. Thus, brush surfaces, folds, interlayers or other shapes or structures eliciting a foreign body response are avoided. Moreover, the device-forming materials are sufficiently pure to insure that unwanted substances do not leach out from the device materials themselves. Additionally, following device preparation, the treatment of the external surface of the device with fluids or materials (e.g. serum) which may adhere to or be absorbed by the device and subsequently impair device biocompatibility is avoided.

First, the materials used to form the device jacket are substances selected based upon their ability to be compatible with, and accepted by, the tissues of the recipient of the implanted device. Substances are used which are not harmful to the recipient or to the isolated cells. Preferred substances include polymer materials, i.e., thermoplastic polymers. Particularly preferred thermoplastic polymer substances are those which are modestly hydrophobic, i.e. those having a solubility parameter as defined in Brandrup J., et al. Polymer Handbook 3rd Ed., John Wiley & Sons, NY (1989), between 8 and 15, or more preferably, between 9 and 14 $(Joules/m^3)^{1/2}$. The polymer substances are chosen to have a solubility parameter low enough so that they are soluble in organic solvents and still high enough so that they will partition to form a proper membrane. Such polymer substances should be substantially free of labile nucleophilic moieties and be highly resistant to oxidants and enzymes even in the absence of stabilizing agents. The period of residence in vivo which is contemplated for the particular vehicle must also be considered: substances must be chosen which are adequately stable when exposed to physiological conditions and stresses. Many thermoplastics are known which are sufficiently stable, even for extended periods of residence in vivo, such as periods in excess of one or two years.

The choice of materials used to construct the device is determined by a number of factors as described in detail in Dionne WO 92/19195, herein incorporated by reference. Briefly, various polymers and polymer blends can be used to manufacture the capsule jacket. Polymeric membranes forming the device and the growth surfaces therein may include polyacrylates (including acrylic copolymers), polyvinylidenes, polyvinyl chloride copolymers, polyurethanes, polystyrenes, polyamides, polymethylmethacrylate, polyvinyldifluoride, polyolefins, cellulose acetates, cellulose nitrates, polysulfones, polyphosphazenes, polyacrylonitriles, poly(acrylonitrile/covinyl chloride), as well as derivatives, copolymers and mixtures thereof.

A preferred membrane casting solution comprises a either polysulfone dissolved in the water-miscible solvent dimethylacetamide (DMACSO) or polyethersulfone dissolved in the water-miscible solvent butyrolactone. This casting solution can optionally comprise hydrophilic or hydrophobic additives which affect the permeability characteristics of the finished membrane. A preferred hydrophilic additive for the polysulfone or polyethersulfone is polyvinylpyrrolidone (PVP). Other suitable polymers comprise polyacrylonitrile (PAN), polymethylmethacrylate (PMMA), polyvinyldifluoride (PVDF), polyethylene oxide, polyolefins (e.g., polyisobutylene or polypropylene), polyacrylonitrile/polyvinyl chloride (PAN/PVC), and/or cellulose derivatives (e.g., cellulose acetate or cellulose butyrate). Compatible water-miscible solvents for these and other suitable polymers and copolymers are found in the teachings of U.S. Pat. No. 3,615,024.

Second, substances used in preparing the biocompatible jacket of the device are either free of leachable pyrogenic or otherwise harmful, irritating, or immunogenic substances or are exhaustively purified to remove such harmful substances. Thereafter, and throughout the manufacture and maintenance of the device prior to implantation, great care is taken to prevent the adulteration or contamination of the device or jacket with substances, which would adversely affect its biocompatibility.

Third, the exterior configuration of the device, including its texture, is formed in such a manner that it provides an optimal interface with the eye of the recipient after implantation. Certain device geometries have also been found to specifically elicit foreign body fibrotic responses and should be avoided. Thus, devices should not contain structures having interlayers such as brush surfaces or folds. In general, opposing vehicle surfaces or edges either from the same or adjacent vehicles should be at least 1 mm apart, preferably greater than 2 mm and most preferably greater than 5 mm. Preferred embodiments include cylinders having an outer diameter of between about 200 and 1600 µm and a length between about 0.4 and 1 mm. Preferably, the core of the devices has a volume of approximately between 2 µl and 20 µl. However, those skilled in the art will recognize that it is also possible to use "micronized" devices having a core volume of less than 0.5 µl (e.g., about 0.3 µl).

The surrounding jacket of the biocompatible devices can optionally include substances which decrease or deter local inflammatory response to the implanted vehicle and/or generate or foster a suitable local environment for the implanted cells or tissues. For example antibodies to one or more mediators of the immune response could be included. Available potentially useful antibodies such as antibodies to the lymphokines tumor necrosis factor (TNF), and to interferons (IFN) can be included in the matrix precursor solution. Similarly, an anti-inflammatory steroid can be included. See Christenson, L., et al., J. Biomed. Mat. Res., 23, pp. 705-718 (1989); Christenson, L., Ph.D. thesis, Brown University, 1989, herein incorporated by reference. Alternatively, a substance which stimulates angiogenesis (ingrowth of capillary beds) can be included.

In some embodiments, the jacket of the present device is immunoisolatory and/or immunoprotective. That is, it protects cells in the core of the device from the immune system of the individual in whom the device is implanted. It does so (1) by preventing harmful substances of the individual's body from entering the core, (2) by minimizing contact between the individual and inflammatory, antigenic, or otherwise harmful materials which may be present in the core and (3) by providing a spatial and physical barrier sufficient to prevent immunological contact between the isolated moiety and detrimental portions of the individual's immune system.

In some embodiments, the external jacket may be either an ultrafiltration membrane or a microporous membrane. Those skilled in the art will recognize that ultrafiltration membranes are those having a pore size range of from about 1 to about 100 nanometers while a microporous membrane has a range of between about 1 to about 10 microns.

The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thicknesses of 20 to 50 or 20 to 75 microns are particularly preferred. In one preferred embodiment, the semi-permeable membrane is between 90 and 120 µm thick. Types of immunological attack which can be prevented or minimized by the use of the instant device include attack by macrophages, neutrophils, cellular immune responses (e.g. natural killer cells and antibody-dependent T cell-mediated cytolysis (ADCC)), and humoral response (e.g. antibody-dependent complement mediated cytolysis).

The capsule jacket may be manufactured from various polymers and polymer blends including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Capsules manufactured from such materials are described, e.g., in U.S. Pat. Nos. 5,284,761 and 5,158,881, incorporated herein by reference. Capsules formed from a polyether sulfone (PES) fiber, such as those described in U.S. Pat. Nos. 4,976,859 and 4,968,733, incorporated herein by reference, may also be used.

Depending on the outer surface morphology, capsules have been categorized as Type 1 (T1), Type 2 (T2), Type 1/2 (T1/2), or Type 4 (T4). Such membranes are described, e.g., in Lacy et al., "Maintenance Of Normoglycemia In Diabetic Mice By Subcutaneous Xenografts Of Encapsulated Islets", Science, 254, pp. 1782-84 (1991), Dionne et al., WO 92/19195 and Baetge, WO 95/05452. A smooth outer surface morphology is preferred.

Those skilled in the art will recognize that capsule jackets with permselective, immunoisolatory membranes are preferable for sites that are not immunologically privileged. In contrast, microporous membranes or permselective membranes may be suitable for immunologically privileged sites. For implantation into immunologically privileged sites, capsules made from the PES or PS membranes are preferred.

Any suitable method of sealing the capsules know in the art may be used, including the employment of polymer adhesives and/or crimping, knotting and heat sealing. In addition, any suitable "dry" sealing method can also be used. In such methods, a substantially non-porous fitting is provided through which the cell-containing solution is introduced. Subsequent to filling, the capsule is sealed. Such methods are described in, e.g., U.S. Pat. Nos. 5,653,688; 5,713,887; 5,738,673; 6,653,687; 5,932,460; and 6,123,700, which are herein incorporated by reference. In one preferred method, the ends of the device are sealed using methyl methacrylate.

Other molecules may be co-delivered in addition to the biologically active molecules described herein. For example, it may be preferable to deliver trophic factor(s) with an anti-angiogenic factor.

Co-delivery can be accomplished in a number of ways. In this example, antibody and antibody fragments require constructs encoding light and heavy chain sequences. First, cells may be transfected with separate constructs containing the genes encoding the described molecules. Second, cells may be transfected with a single construct containing two or more genes as well as the necessary control elements. Third, two or more separately engineered cell lines can be either co-encapsulated or more than one device can be implanted at the site of interest.

For some indications, it may be preferable to deliver BAMs to two different sites in the eye concurrently. Neurotrophic factors or biologically active molecules can be delivered in the intravitreal space to reach the inner retina and periocularly in order to go transcleral to reach the choroid and the outer retina (e.g., the retinal pigment epithelial (RPE) cells and photoreceptors). However, those skilled in the art will recognize that intravitreal delivery can also reach the outer retina.

Also contemplated is the use of different cell types during the course of the treatment regime. For example, a patient may be implanted with a capsule device containing a first cell type (e.g., BHK cells). If after time, the patient develops an immune response to that cell type, the capsule can be retrieved, or explanted, and a second capsule can be implanted containing a second cell type (e.g., CHO cells). In this manner, continuous provision of the therapeutic molecule is possible, even if the patient develops an immune response to one of the encapsulated cell types.

The methods and devices described herein are intended for use in a primate, preferably human host, recipient, patient, subject or individual. A number of different ocular implantation sites are contemplated for the devices and methods described herein. Suitable implantation sites include, but are not limited to, the aqueous and vitreous humors of the eye, the periocular space, the anterior chamber, and/or the Subtenon's capsule. Within the body, implantation sites may include subcutaneous, or intraperitoneal. In addition, implantation may be directed at localized delivery at or near lesions requiring the desired biologic therapy. Example of such disease sites may be inflamed joints and/or sites of benign or malignant tumors. Access by the device to the circulatory system can further extend the range of potential disease sites within the body to distally affected organs and tissues.

The type and extent of immunological response by the recipient to the implanted device will be influenced by the relationship of the recipient to the isolated cells within the core. For example, if core contains syngeneic cells, these will not cause a vigorous immunological reaction, unless the recipient suffers from an autoimmunity with respect to the particular cell or tissue type within the device. Syngeneic cells or tissue are rarely available. In many cases, allogeneic or xenogeneic cells or tissue (i.e., from donors of the same species as, or from a different species than, the prospective recipient) may be available. The use of immunoisolatory devices allows the implantation of allogeneic or xenogeneic cells or tissue, without a concomitant need to immunosuppress the recipient. Use of immunoisolatory capsules also allows the use of unmatched cells (allographs). Therefore, the instant device makes it possible to treat many more individuals than can be treated by conventional transplantation techniques.

The type and vigor of an immune response to xenografted tissue is expected to differ from the response encountered when syngeneic or allogeneic tissue is implanted into a recipient. This rejection may proceed primarily by cell-mediated, or by complement-mediated attack. The exclusion of IgG from the core of the vehicle is not the touchstone of immunoprotection, because in most cases IgG alone is insufficient to produce cytolysis of the target cells or tissues. Using immunoisolatory devices, it is possible to deliver needed high molecular weight products or to provide metabolic functions pertaining to high molecular weight substances, provided that critical substances necessary to the mediation of immunological attack are excluded from the immunoisolatory capsule. These substances may comprise the complement attack complex component Clq, or they may comprise phagocytic or cytotoxic cells. Use of immunoisolatory capsules provides a protective barrier between these harmful substances and the isolated cells.

While the devices described herein are macrocapsules, those skilled in the art will recognize that microcapsules such as, for example those described in Rha, Lim, and Sun may also be used. (See, Rha, C. K. et al., U.S. Pat. No. 4,744,933; Methods in Enzymology 137, pp. 575-579 (1988); U.S. Pat. Nos. 4,652,833; 4,409,331). In general, microcapsules differ from macrocapsules by (1) the complete exclusion of cells from the outer layer of the device, and (2) the thickness of the outer layer of the device. Typically, microcapsules have a volume on the order of 1 µl and contain fewer than $10^4$ cells. More specifically, microencapsulation encapsulates approximately 500-50,000 cells, generally, per capsule.

Capsules with a lower MWCO may be used to further prevent interaction of molecules of the patient's immune system with the encapsulated cells.

Any of the devices used in accordance with the methods described herein must provide, in at least one dimension, sufficiently close proximity of any isolated cells in the core to the surrounding eye tissues of the recipient in order to maintain the viability and function of the isolated cells. However, the diffusional limitations of the materials used to form the device do not in all cases solely prescribe its configurational limits. Certain additives can be used which alter or enhance the diffusional properties, or nutrient or oxygen transport properties, of the basic vehicle. For example, the internal medium of the core can be supplemented with oxygen-saturated perfluorocarbons, thus reducing the needs for immediate contact with blood-borne oxygen. This will allow isolated cells or tissues to remain viable while, for instance, a gradient of angiotensin is released from the vehicle into the surrounding tissues, stimulating ingrowth of capillaries. References and methods for use of perfluorocarbons are given by Faithful, N. S. Anaesthesia, 42, pp. 234-242 (1987) and NASA Tech Briefs MSC-21480, U.S. Govt. Printing Office, Washington, D.C. 20402, incorporated herein by reference. Alternatively for clonal cell lines such as PC12 cells, genetically engineered hemoglobin sequences may be introduced into the cell lines to produce superior oxygen storage. See NPO-17517 NASA Tech Briefs, 15, p. 54.

The encapsulated cells can further be primed for enhanced secretion by environmental control and macronutrient and micronutrient supplementation. It is well known in the field of upstream development of recombinant cells that optimizing culture media, pH and temperature can have profound effects on cellular growth, density and recombinant protein output. Cells and ECT devices primed in such manner may increase productivity upon implantation into the host, allowing a prolonged enhanced productivity phenotype which may be useful for therapy. As examples, such nutrient compounds could be, but not limited to Tris, HEPES, glucose, sucrose, phospholipids, cholesterol, ascorbic acid, magnesium, sodium, vitamins, potassium, and calcium, cellular conditioned media, fetal calf serum, albumin, lecithin, sphingomyelin, lipoproteins, HDL, LDL, polyamines, ethanolamines, fibronectin, transferring, laminin, cholera toxins, hydrocortisone and other steroids, prostaglandins, insulin, EGF, FGF2 and other growth factors, dexamethasone, beta-mercaptoethanol and other reducing agents, and selenium. In addition, pre-formulated media may be used from commercial media suppliers such as Biowhittaker, Gibco/Invitrogen, Hyclone, JRH, Expression Systems, Sigma, PAA and Irvine Scientific.

The thickness of the device jacket should be sufficient to prevent an immunoresponse by the patient to the presence of the devices. For that purpose, the devices preferably have a minimum thickness of 1 µm or more and are free of the cells.

Additionally, reinforcing structural elements can also be incorporated into the devices. For example, these structural elements can be made in such a fashion that they are impermeable and are appropriately configured to allow tethering or suturing of the device to the eye tissues of the recipient. In certain circumstances, these elements can act to securely seal the jacket (e.g., at the ends of the cylinder), thereby completing isolation of the core materials (e.g., a molded thermoplastic clip). In many embodiments, it is desirable that these structural elements should not occlude a significant area of the permselective jacket.

The device described herein is of a sufficient size and durability for complete retrieval after implantation. One preferred device has a core of a volume of approximately 1-3 uL. The internal geometry of micronized devices has a volume of approximately 0.05-0.1 uL.

Along with the biologically active molecules described herein, at least one additional BAM can also be delivered from the device to the eye. For example, the at least one additional BAM can be provided from a cellular or a noncellular source. When the at least one additional BAM is provided from a noncellular source, the additional BAM(s) may be encapsulated in, dispersed within, or attached to one or more components of the cell system including, but not limited to: (a) sealant; (b) scaffold; (c) jacket membrane; (d) tether anchor; and/or (e) core media. In such embodiment, co-delivery of the BAM from a noncellular source may occur from the same device as the BAM from the cellular source.

Alternatively, two or more encapsulated cell systems can be used. For example, the least one additional biologically active molecule can be a nucleic acid, a nucleic acid fragment, a peptide, a polypeptide, a peptidomimetic, a carbohydrate, a lipid, an organic molecule, an inorganic molecule, a therapeutic agent, or any combinations thereof. Specifically, the therapeutic agents may be a neuronal survival cytokine, an anti-angiogenic drug, a steroidal and non-steroidal anti-inflammatory drug, an anti-mitotic drug, an anti-tumor drug, an anti-parasitic drug, an IOP reducer, a peptide drug, and/or any other biologically active molecule drugs approved for commercial use.

Suitable excipients include, but are not limited to, any non-degradable or biodegradable polymers, hydrogels, solubility enhancers, hydrophobic molecules, proteins, salts, or other complexing agents approved for formulations.

Non-cellular dosages can be varied by any suitable method known in the art such as varying the concentration of the therapeutic agent, and/or the number of devices per eye, and/or modifying the composition of the encapsulating excipient. Cellular dosage can be varied by changing (1) the number of cells per device, (2) the number of devices per eye, and/or (3) the level of BAM production per cell. Cellular production can be varied by changing, for example, the copy number of the gene for the BAM in the transduced cell, or the efficiency of the promoter driving expression of the BAM. Suitable dosages from cellular sources may range from about 1 pg to about 1000 mg per day.

Also provided are methods for making the macrocapsular devices described herein. Devices may be formed by any suitable method known in the art. (See, e.g., U.S. Pat. Nos. 6,361,771; 5,639,275; 5,653,975; 4,892,538; 5,156,844; 5,283,138; and 5,550,050, each of which is incorporated herein by reference).

Membranes used can also be tailored to control the diffusion of molecules, such as the biologically active molecule, based on their molecular weight. (See Lysaght et al., 56 J. Cell Biochem. 196 (1996), Colton, 14 Trends Biotechnol. 158 (1996)). Using encapsulation techniques, cells can be transplanted into a host without immune rejection, either with or without use of immunosuppressive drugs. The capsule can be made from a biocompatible material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors. Numerous biocompatible materials are known, having various outer surface morphologies and other mechanical and structural characteristics.

If a device with a jacket of thermoplastic or polymer membrane is desired, the pore size range and distribution can be determined by varying the solids content of the solution of precursor material (the casting solution), the chemical composition of the water-miscible solvent, or optionally including a hydrophilic or hydrophobic additive to the casting solution, as taught by U.S. Pat. No. 3,615,024. The pore size may also be adjusted by varying the hydrophobicity of the coagulant and/or of the bath.

Typically, the casting solution will comprise a polar organic solvent containing a dissolved, water-insoluble polymer or copolymer. This polymer or copolymer precipitates upon contact with a solvent-miscible aqueous phase, forming a permselective membrane at the site of interface. The size of pores in the membrane depends upon the rate of diffusion of the aqueous phase into the solvent phase; the hydrophilic or hydrophobic additives affect pore size by altering this rate of diffusion. As the aqueous phase diffuses farther into the solvent, the remainder of the polymer or copolymer is precipitated to form a trabecular support which confers mechanical strength to the finished device.

The external surface of the device is similarly determined by the conditions under which the dissolved polymer or copolymer is precipitated (i.e., exposed to the air, which generates an open, trabecular or sponge-like outer skin, immersed in an aqueous precipitation bath, which results in a smooth permselective membrane bilayer, or exposed to air saturated with water vapor, which results in an intermediate structure).

The surface texture of the device is dependent in part on whether the extrusion nozzle is positioned above, or immersed in, the bath: if the nozzle is placed above the surface of the bath a roughened outer skin will be formed, whereas if the nozzle is immersed in the bath a smooth external surface is formed.

The surrounding or peripheral matrix or membrane can be preformed, filled with the materials which will form the core (for instance, using a syringe), and subsequently sealed in such a manner that the core materials are completely enclosed. The device can then be exposed to conditions which bring about the formation of a core matrix if a matrix precursor material is present in the core.

The devices can provide for the implantation of diverse cell or tissue types, including fully-differentiated, anchorage-dependent, fetal or neonatal, or transformed, anchorage-independent cells or tissue. The cells to be isolated are prepared either from a donor (i.e., primary cells or tissues, including adult, neonatal, and fetal cells or tissues) or from cells which replicate in vitro (i.e., immortalized cells or cell lines, including genetically modified cells). In all cases, a sufficient quantity of cells to produce effective levels of the needed product or to supply an effective level of the needed metabolic function is prepared, generally under sterile conditions, and maintained appropriately (e.g. in a balanced salt solution such as Hank's salts, or in a nutrient medium, such as Ham's F12) prior to isolation.

The ECT devices are of a shape which tends to reduce the distance between the center of the device and the nearest portion of the jacket for purposes of permitting easy access of nutrients from the patient into the cell or of entry of the patient's proteins into the cell to be acted upon by the cell to provide a metabolic function. In that regard, a non-spherical shape, such as a cylinder, is preferred.

Four important factors that influence the number of cells or amount of tissue to be placed within the core of the device (i.e., loading density) are: (1) device size and geometry; (2) mitotic activity within the device; (3) viscosity requirements for core preparation and or loading; and (4) pre-implantation assay and qualification requirements.

With respect to the first of these factors, (device size and geometry), the diffusion of critical nutrients and metabolic requirements into the cells as well as diffusion of metabolites away from the cell are critical to the continued viability of the cells. In the case of RPE cells such as ARPE-19 cells, the neighboring cells are able to phagocytize the dying cells and use the debris as an energy source.

Among the metabolic requirements met by diffusion of substances into the device is the requirement for oxygen. The oxygen requirements of the specific cells must be determined for the cell of choice. See Methods and references for determination of oxygen metabolism are given in Wilson D. F. et al., J. Biol. Chem., 263, pp. 2712-2718, (1988).

With respect to the second factor (cell division), if the cells selected are expected to be actively dividing while in the device, then they will continue to divide until they fill the available space, or until phenomena such as contact inhibition limit further division. For replicating cells, the geometry and size of the device will be chosen so that complete filling of the device core will not lead to deprivation of critical nutrients due to diffusional limitations.

With respect to the third factor (viscosity of core materials) cells in densities occupying up to 70% of the device volume can be viable, but cell solutions in this concentration range would have considerable viscosity. Introduction of cells in a very viscous solution into the device could be prohibitively difficult. In general, for both two step and coextrusion strategies, cell loading densities of higher than 30% will seldom be useful, and in general optimal loading densities will be 20% and below. For example, for fragments of tissues, it is important, in order to preserve the viability of interior cells, to observe the same general guidelines as above and tissue fragments should not exceed 250 microns in diameter with the interior cells having less than 15, preferably less than 10 cells between them and the nearest diffusional surface.

Finally, with respect to the fourth factor (preimplantation and assay requirements), in many cases, a certain amount of time will be required between device preparation and implantation. For instance, it may be important to qualify the device in terms of its biological activity. Thus, in the case of mitotically active cells, preferred loading density will also consider the number of cells which must be present in order to perform the qualification assay.

In most cases, prior to implantation in vivo, it will be important to use in vitro assays to establish the efficacy of the BAM (e.g., the neuronal survival cytokine, such as CNTF) within the device. Devices can be constructed and analyzed using model systems in order to allow the determination of the efficacy of the vehicle on a per cell or unit volume basis.

Following these guidelines for device loading and for determination of device efficacy, the actual device size for implantation will then be determined by the amount of biological activity required for the particular application. The number of devices and device size should be sufficient to produce a therapeutic effect upon implantation and is determined by the amount of biological activity required for the particular application. In the case of secretory cells releasing therapeutic substances, standard dosage considerations and criteria known to the art will be used to determine the amount of secretory substance required. Factors to be considered include the size and weight of the recipient; the productivity or functional level of the cells; and, where appropriate, the normal productivity or metabolic activity of the organ or tissue whose function is being replaced or augmented. It is also important to consider that a fraction of the cells may not survive the immunoisolation and implantation procedures. Moreover, whether the recipient has a preexisting condition which can interfere with the efficacy of the implant must also be considered. Devices described herein can easily be manufactured which contain many thousands of cells. For example, current ophthalmic clinical devices contain between 200,000 and 750,000 cells, whereas micronized devices would contain between 10,000 and 100,000 cells. Other large scale devices may contain between 1,000,000 to 100,000,000 cells.

Encapsulated cell therapy is based on the concept of isolating cells from the recipient host's immune system by surrounding the cells with a semipermeable biocompatible material before implantation within the host. For example, devices in which genetically engineered ARPE-19 cells are encapsulated in an immunoisolatory capsule, which, upon implantation into a recipient host, minimizes the deleterious effects of the host's immune system on the ARPE-19 cells in the core of the device are described. ARPE-19 cells are immunoisolated from the host by enclosing them within implantable polymeric capsules formed by a microporous membrane. This approach prevents the cell-to-cell contact between the host and implanted tissues, thereby eliminating antigen recognition through direct presentation.

Any of the biologically active molecules described herein (alone or in any combination) can be delivered intraocularly (e.g., in the anterior chamber and the vitreous cavity), periocularly (e.g., within or beneath Tenon's capsule), or both. The devices may also be used to provide controlled and sustained release of the biologically active molecules to treat various ophthalmic disorders, ophthalmic diseases, and/or other diseases which have ocular effects.

Intraocular (preferably in the vitreous) or per ocular (preferably in the sub-Tenon's space or region) delivery of any of the biologically active molecules described herein, in a dosage range of 0.1 pg and 1000 μg (e.g., between 0.1 pg and 500 μg; between 0.1 pg and 250 μg; between 0.1 pg and 100 μg; between 0.1 pg and 50 μg; between 0.1 pg and 25 μg; between 0.1 pg and 10 μg; between 0.1 pg and 5 μg; between 0.1 pg and 100 ng; between 0.1 pg and 50 ng; between 0.1 pg and 25 ng; between 0.1 pg and 10 ng; or between 0.1 pg and 5 ng) per eye per patient per day is contemplated. In one non-limiting example, the therapeutic amount is at least 0.5-50 μg/ml steady state in the eye. Suitable therapeutic amounts may include, for example, 0.5 ug, 0.6 ug, 0.7 ug, 0.8 ug, 0.9 ug, 1 ug, 2 ug, 3 ug, 4 ug, 5 ug, 6 ug, 7 ug, 8 ug, 9 ug, 10 ug, 11 ug, 12 ug, 13 ug, 14 ug, 15 ug, 16 ug, 17 ug, 18 ug, 19 ug, 20 ug, 21 ug, 22 ug, 23 ug, 24 ug, 25 ug, 26 ug, 27 ug, 28 ug, 29 ug, 30 ug, 31 ug, 32 ug, 33 ug, 34 ug, 35 ug, 36 ug, 37 ug, 38 ug, 39 ug, 40 ug, 41 ug, 42 ug, 43 ug, 44 ug, 45 ug, 46 ug, 47 ug, 48 ug, 49 ug, 50 ug, 51 ug, 52 ug, 53 ug, 54 ug, 55 ug, 56 ug, 57 ug, 58 ug, 59 ug, 60 ug, 61 ug, 62 ug, 63 ug, 64 ug, 65 ug, 66 ug, 67 ug, 68 ug, 69 ug, 70 ug, 71 ug, 72 ug, 73 ug, 74 ug, 75 ug, 76 ug, 77 ug, 78 ug, 79 ug, 80 ug, 81 ug, 82 ug, 83 ug, 84 ug, 85 ug, 86 ug, 87 ug, 88 ug, 89 ug, 90 ug, 91 ug, 92 ug, 93 ug, 94 ug, 95 ug, 96 ug, 97 ug, 98 ug, 99 ug, 100 ug, 150 ug, 200 ug, 250 ug, 300 ug, 350 ug, 400 ug, 450 ug, 500 ug, 550 ug, 600 ug, 650 ug, 700 ug, 750 ug, 800 ug, 850 ug, 900 ug, 950 ug, 1000 ug. Moreover, the cells lines and devices described herein are able to express this therapeutic amount for a period of at least two years.

Ophthalmic disorders that may be treated include, but are not limited to glaucoma, retinitis pigmentosa, geographic atrophy, age-related macular degeneration, and other acquired disorders, macular telangiectasia, diabetic retinopathies, diabetic macular edema, proliferative retinopathies, retinal vascular diseases, vascular anomalies, age-related macular degeneration and other acquired disorders, endophthalmitis, infectious diseases, inflammatory but non-infectious diseases, AIDS-related disorders, ocular ischemia syndrome, pregnancy-related disorders, peripheral retinal degenerations, retinal degenerations, toxic retinopathies, retinal tumors, choroidal tumors, choroidal disorders, vitreous disorders, retinal detachment and proliferative vitreoretinopathy, non-penetrating trauma, penetrating trauma, post-cataract complications, and inflammatory optic neuropathies.

Those skilled in the art will recognized that age-related macular degeneration includes, but is not limited to, wet and dry age-related macular degeneration, exudative age-related macular degeneration, and myopic degeneration.

In some embodiments, the disorders to be treated are primarily neurodegenerative such as glaucoma, RP, geographic atrophy, or macular telangiectasia. In other embodiments, the disorder to be treated is primarily neovascular, such as wet AMD, but results in an injury of the neural tissues. For example, retinal ischemia-associated ocular neovascularization is a major cause of blindness in diabetes and many other diseases.

The devices and cell lines may also be used to treat conditions relating to other intraocular neovascularization-based diseases. For example, such neovascularization can occur in diseases such as diabetic retinopathy, central retinal vein occlusion and, possibly, age-related macular degeneration. Corneal neovascularization is a major problem because it interferes with vision and predisposes patients to corneal graft failure. A majority of severe visual loss is associated with disorders that result in ocular neovascularization. The devices and cell lines described herein may also be used to treat other ophthalmic disorders that are characterized by elevated intraocular pressure (TOP), such as, for example, glaucoma.

The use of the devices and techniques described herein provide several advantages over other delivery routes: the biologically active molecules can be delivered to the eye directly, which reduces or minimizes unwanted peripheral side effects and very small doses of the biologically active molecule (i.e., nanogram or low microgram quantities rather than milligrams) can be delivered compared with topical applications, thereby also potentially lessening side effects. Moreover, since viable cells continuously produce newly synthesized biologically active molecules, these techniques should be superior to injection delivery of the biologically active molecule, where the dose fluctuates greatly between injections and the biologically active molecule is continuously degraded but not continuously replenished.

Living cells and cell lines genetically engineered to secrete the biologically active molecules can be encapsulated in the device and surgically inserted (under retrobulbar anesthesia) into any appropriate anatomical structure of the eye. For example, the devices can be surgically inserted into the vitreous of the eye, where they are preferably tethered to the sclera to aid in removal. Devices can remain in the vitreous as long as necessary to achieve the desired prophylaxis or therapy. For example, the desired therapy may include promotion of neuron or photoreceptor survival or repair, or inhibition and/or reversal of retinal or choroidal neovascularization, as well as inhibition of uveal, retinal and optic nerve inflammation. With vitreal placement, the biologically active molecule, may be delivered to the retina or the retinal pigment epithelium (RPE).

The device can be implanted in the vitreous, the aqueous humor, the Subtenon's space, the periocular space, the posterior chamber or the anterior chamber of the eye.

By way of non-limiting example, the device can be inserted as follows for RP, geographic atrophy, and macular telangiectasia subjects. The device is implanted under retrobulbar anesthesia using bupivacaine at a 1:1 mixture with 4% lidocaine. The implant is inserted through a 2.0 mm sclerotomy made 3.75 mm posterior to the limbus in the inferotemporal quadrant and anchored with a single suture. Two additional sutures are applied to facilitate the wound closure. A subconjunctival antibiotic injection of 100 mg of cefazolin is given at the conclusion of surgery, and topical 1% prednisolone acetate and ciprofloxacin drops are given daily over the following week.

For glaucoma subjects, the implantation procedure is as described above, with the exception that the device is inserted through the pars plana and secured to the scleral closure.

In other embodiments, cell-loaded devices are implanted periocularly, within or beneath the space known as Tenon's capsule, which is less invasive than implantation into the vitreous. Therefore, complications such as vitreal hemorrhage and/or retinal detachment are potentially eliminated. This route of administration also permits delivery of the biologically active molecules described herein to the RPE or the retina. Periocular implantation is especially preferred for treating choroidal neovascularization and inflammation of the optic nerve and uveal tract. In general, delivery from periocular implantation sites will permit circulation of the biologically active molecules to the choroidal vasculature, retinal vasculature, and the optic nerve.

Delivery of biologically active molecules directly to the choroidal vasculature (periocularly) or to the vitreous (intraocularly) using the devices and methods described herein may reduce or alleviate the problems associated with prior art treatment methods and devices and may permit the treatment of poorly defined or occult choroidal neovascularization as well as provide a way of reducing or preventing recurrent choroidal neovascularization via adjunctive or maintenance therapy.

Genetically engineered ARPE-19 cells that secrete either high or low doses of a BAM such as CNTF are encapsulated into an ECT device that is subsequently implanted into subjects suffering from an ophthalmic disorder characterized by aberrant angiogenesis, inflammation, retinal degeneration, or any combination thereof. Surprisingly, ECT devices have been shown to secrete therapeutically effective amounts of the BAM for at least two years post implantation. For example, CNTF-secreting ECT devices have been shown to secrete CNTF for a mean residence time of up to 47 months post implantation.

Implantation of the biocompatible devices is performed under sterile conditions. The device can be implanted using a syringe or any other method known to those skilled in the art. Generally, the device is implanted at a site in the recipient's body which will allow appropriate delivery of the secreted product or function to the recipient and of nutrients to the implanted cells or tissue, and will also allow access to the device for retrieval and/or replacement. A number of different implantation sites are contemplated. These include, e.g., the aqueous humor, the vitreous humor, the sub-Tenon's capsule, the periocular space, and the anterior chamber. Preferably, for implant sites that are not immunologically privileged, such as periocular sites, and other areas outside the anterior chamber (aqueous) and the posterior chamber (vitreous), the capsules are immunoisolatory.

It is preferable to verify that the cells immobilized within the device function properly both before and after implantation. Any assays or diagnostic tests well known in the art can be used for these purposes. For example, an ELISA (enzyme-linked immunosorbant assay), chromatographic or enzymatic assay, or bioassay specific for the secreted product can be used. If desired, secretory function of an implant can be monitored over time by collecting appropriate samples (e.g., serum) from the recipient and assaying them.

The use of many of the prior art devices and surgical techniques resulted in a large number of retinal detachments. The occurrence of this complication is lessened because the devices and methods described herein are less invasive compared to several other therapies.

Modified, truncated and/or mutein forms of the biologically active molecules described herein can also be used. Further, the use of active fragments of these biologically active molecules (i.e., those fragments having biological activity sufficient to achieve a therapeutic effect) is also contemplated. Also contemplated are biologically active molecules modified by attachment of one or more polyethylene glycol (PEG) or other repeating polymeric moieties as well as combinations of these proteins and polycistronic versions thereof.

Treatment of many conditions according to the methods described herein will require only one or at most less than 50 implanted devices per eye to supply an appropriate therapeutic dose. Therapeutic dosages may be between about 0.1 pg and 1000 μg per eye per patient per day (e.g., between 0.1 pg and 500 μg; between 0.1 pg and 250 μg, between 0.1 pg and 100 μg; between 0.1 pg and 50 μg; between 0.1 pg and 25 μg; between 0.1 pg and 10 μg; between 0.1 pg and 5 μg; between 0.1 pg and 100 ng; between 0.1 pg and 50 ng; between 0.1 pg and 25 ng; between 0.1 pg and 10 ng; or between 0.1 pg and 5 ng per eye per patient per day). In one non-limiting example, the therapeutic amount is at least 0.5-50 μg/ml steady state in the eye. Suitable therapeutic amounts may include, for example, 0.5 ug, 0.6 ug, 0.7 ug, 0.8 ug, 0.9 ug, 1 ug, 2 ug, 3 ug, 4 ug, 5 ug, 6 ug, 7 ug, 8 ug, 9 ug, 10 ug, 11 ug, 12 ug, 13 ug, 14 ug, 15 ug, 16 ug, 17 ug, 18 ug, 19 ug, 20 ug, 21 ug, 22 ug, 23 ug, 24 ug, 25 ug, 26 ug, 27 ug, 28 ug, 29 ug, 30 ug, 31 ug, 32 ug, 33 ug, 34 ug, 35 ug, 36 ug, 37 ug, 38 ug, 39 ug, 40 ug, 41 ug, 42 ug, 43 ug, 44 ug, 45 ug, 46 ug, 47 ug, 48 ug, 49 ug, 50 ug, 51 ug, 52 ug, 53 ug, 54 ug, 55 ug, 56 ug, 57 ug, 58 ug, 59 ug, 60 ug, 61 ug, 62 ug, 63 ug, 64 ug, 65 ug, 66 ug, 67 ug, 68 ug, 69 ug, 70 ug, 71 ug, 72 ug, 73 ug, 74 ug, 75 ug, 76 ug, 77 ug, 78 ug, 79 ug, 80 ug, 81 ug, 82 ug, 83 ug, 84 ug, 85 ug, 86 ug, 87 ug, 88 ug, 89 ug, 90 ug, 91 ug, 92 ug, 93 ug, 94 ug, 95 ug, 96 ug, 97 ug, 98 ug, 99 ug, 100 ug, 150 ug, 200 ug, 250 ug, 300 ug, 350 ug, 400 ug, 450 ug, 500 ug, 550 ug, 600 ug, 650 ug, 700 ug, 750 ug, 800 ug, 850 ug, 900 ug, 950 ug, 1000 ug. Moreover, the cells lines and devices described herein are able to express this therapeutic amount for a period of at least three months.

Each of the ophthalmic devices described herein is capable of storing between about 1,000 and about 1,000,000 cells, in individual or cluster form, depending on their type.

The invention will be further described in the following examples, which do not limit the scope described in the claims.

EXAMPLES

Example 1

Retinitis Pigmentosa Clinical Trial

Patient Profile and Study Design

Retinitis pigmentosa (RP) patients were recruited to participate in a clinical study in which they would receive a sustained-release, CNTF-secreting ophthalmic ECT device. The study was randomized, double masked, sham-controlled, and performed in multiple research centers (11 participating sites). The RP patients were divided into two study groups: CNTF3 and CNTF4.

The participants in the CNTF3 study group (65 patients) received a one year implant of the CNTF-secreting ECT device. RP patients who were included in the CNTF3 study group were divided into those that received a low-dose (5±0.8 ng/day at implant) CNTF-secreting ECT device (N=22), those that received a high-dose (20±3.0 ng/day at implant) CNTF-secreting ECT device (N=43), and those that received a fellow eye sham suture (N=63). The participants in the CNTF3 study had a best corrected visual acuity (BCVA) of 20/63 to 20/320 prior to receiving the implant. The primary outcome measure for the CNTF3 study was an e-EDTRS best-corrected visual acuity test performed at 12 months post-implant. At the conclusion of the one-year period, the patients were given the option to have the implant removed or to leave the implant in place.

The participants in the CNTF4 study received a two year implant. They were divided into a cohort that received a low-dose (5±0.8 ng/day at implant) CNTF-secreting ECT device (N=20), a high dose (20±3.0 ng/day at implant) CNTF-secreting ECT device (N=48), and all of the participants received a fellow eye sham suture (N=68). The primary outcome measure for the CNTF4 study was a measurement of the visual field sensitivity at twelve months post-implant of the device. At the conclusion of the two-year period, the patients were given the option to have the implant removed or to leave the implant in place.

Sustained Release CNTF-Secreting Device

The CNTF-secreting ECT device used in both the CNTF3 and CNTF4 study is 1 mm in diameter and 6 mm long, constructed of a semi-permeable polymer outer membrane, and contains a medical-grade sealant and a titanium anchor at one end of the device to facilitate suturing to the sclera. The implant was populated with a genetically modified, human retinal pigment epithelial (RPE) cell line (ARPE-19) that was genetically modified to produce human CNTF. Two cell lines resulted from the engineering procedures, each of which secreted different amounts of human CNTF. The devices were loaded with 203,000 genetically engineered cells from either the higher secreting or the lower secreting cell line.

ELISA measurements to detect the quantities of CNTF secreted from each device (i.e. the device loaded with the higher secreting CNTF ARPE-19 cell line and the device loaded with the lower secreting CNTF ARPE-19 cell line) were performed. The data indicated that the devices loaded with the higher secreting CNTF ARPE-19 cell line secreted 20±3.0 ng/day, and the devices loaded with the lower secreting CNTF ARPE-19 cell line secreted 5±0.8 ng/day.

Implantation of the CNTF-Secreting Device

The device was implanted into one eye of the RP patients under retrobulbar anesthesia using bupivacaine at a 1:1 mixture with 4% lidocaine. The implant was inserted through a 2.0 mm sclerotomy made 3.75 mm posterior to the limbus in the inferotemporal quadrant and anchored with a single suture. Two additional sutures were applied to facilitate the wound closure. A subconjunctival antibiotic injection (e.g., 100 mg of cefazolin) was given at the conclusion of surgery, and topical corticosteroid and antibiotic drops (e.g., 1% prednisolone and ciprofloxacin) were given daily over the following week.

12 Months Post-Implant Patient Assessment—CNTF3 Study

Participants in the study were assessed twelve months post implant to ascertain whether any adverse health effects had occurred and to assess various visual and ocular measurements. In particular, participants in the CNTF3 study were assessed for adverse events, including, among other measurements, intraocular pressure increase, retinal detachment, implant extrusion, eye hemorrhage, miosis and cataract presence. Table 1 shows adverse events observed in the CNTF3 study participants.

TABLE 1

Adverse Events/Eye Disorders in RP CNTF3 Trial

| Adverse Events/Eye Disorders | CNTF3 | |
|---|---|---|
| | Low Dose (n = 22) | High Dose (n = 43) |
| Intraocular Pressure Increase* | 0 (0.0%) | 1 (2.3%) |
| Eye Hemorrhage** | 2 (9.1%) | 0 (0.0%) |
| Photopsia | 0 (0.0%) | 1 (2.3%) |
| Miosis | 1 (4.5%) | 11 (25.6%) |
| Cataract*** | 1 (4.5%) | 2 (4.7%) |
| Choroidal Neovascularization | 0 (0.0%) | 0 (0.0%) |
| Wound Leaks or Erosion | 0 (0.0%) | 0 (0.0%) |
| Endophthalmitis | 0 (0.0%) | 0 (0.0%) |
| Implant Extrusion | 0 (0.0%) | 0 (0.0%) |
| Retinal Detachment | 0 (0.0%) | 0 (0.0%) |

*IOP increase (24-31 mmHg) usually lasted a few days to a few weeks and returned to normal at the next scheduled visit without medical intervention.
**Related to the surgical wound and recovered with no sequelae within 10 days.
***Worsening of a pre-existing cataract (mild)

CNTF-3 study participants had their visual acuity assessed 12 months post-implant. The visual acuity test measured the number of letters the study participants were able to identify at the beginning of the study, prior to the implant of the device, and at 12 months following implant of the device. FIG. 1A depicts the number of letters lost 12 months post-implant of the device for participants either receiving a low (5±0.8 ng/day) or a high dose (20±3.0 ng/day) CNTF-secreting device. As depicted in FIG. 1A, study participants who received a high dose secreting device tended to lose fewer letters in comparison to both the sham treated control eye and the low dose device recipients.

Figure 1B:
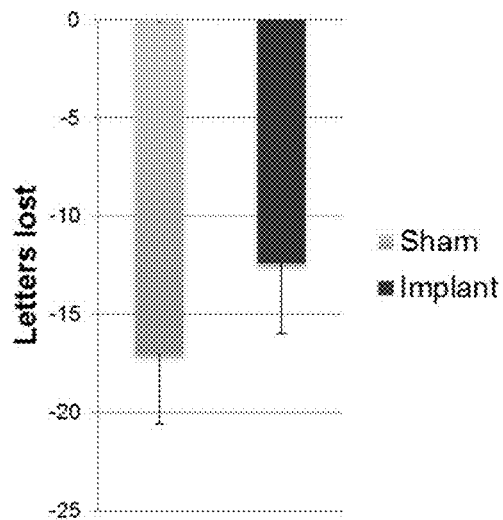

CNTF3 study participants also had their visual acuity assessed 72 months post implant of the device and FIG. 1B depicts the results of the visual acuity test 72 months post implant for CNTF3 study participants. The data indicate that the recipients of the high dose CNTF-secreting implant had statistically fewer letters lost (p=0.006), or maintained better visual acuity, as compared to pooled data from those participants who received a sham condition and those who received the low dose device implant.

Figure 1C:
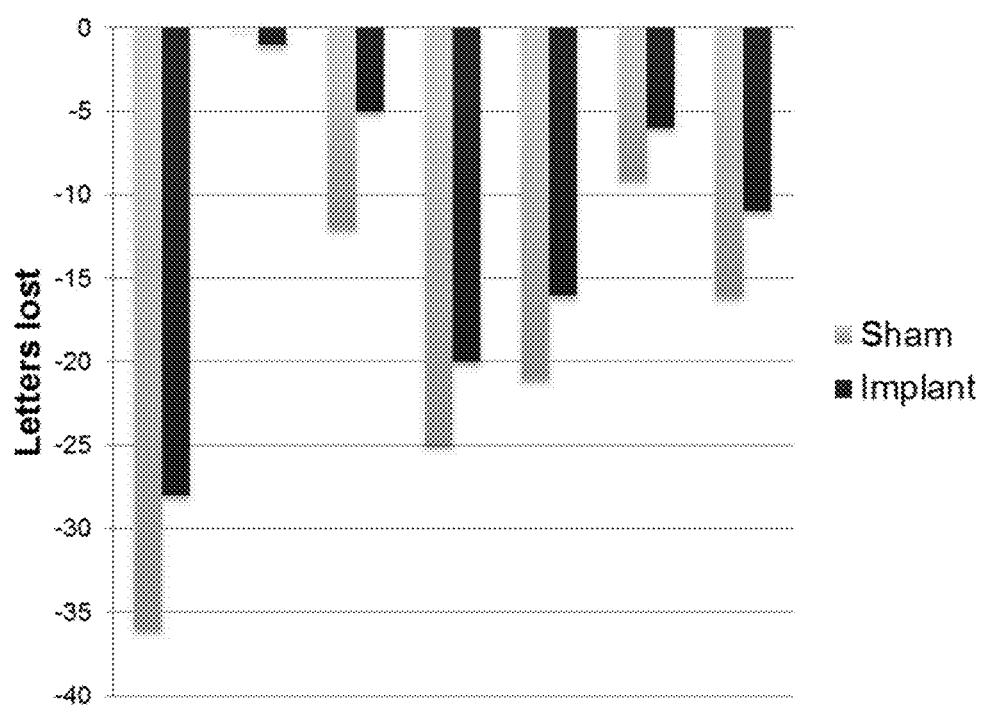

FIG. 1C depicts the results of visual acuity tests on selected individuals. The data collected from this cohort of individuals demonstrates that 6 participants lost fewer letters in the treated eye, whereas 1 study participant had no difference in the number of letters lost at the 72 month, post-implant assessment.

12 Months Post-Implant Patient Assessment—CNTF4 Study

The CNTF4 study participants had their macular volume assessed by stratus optical coherence tomography (stratus OCT) 12 months post-implant of either the low dose (5±0.8 ng/day) or the high dose (20±3.0 ng/day) CNTF-secreting device. FIG. 2 shows the outcome of the stratus OCT measurements of macular volume in the CNTF4 participants 12 months post-implant of the CNTF-secreting device. The data indicate that CNTF4 study participants, both in the low dose and in the high dose cohort had an increase in the macular volume 12 months following implant of the device in comparison to the sham condition eye.

Figure 3A:
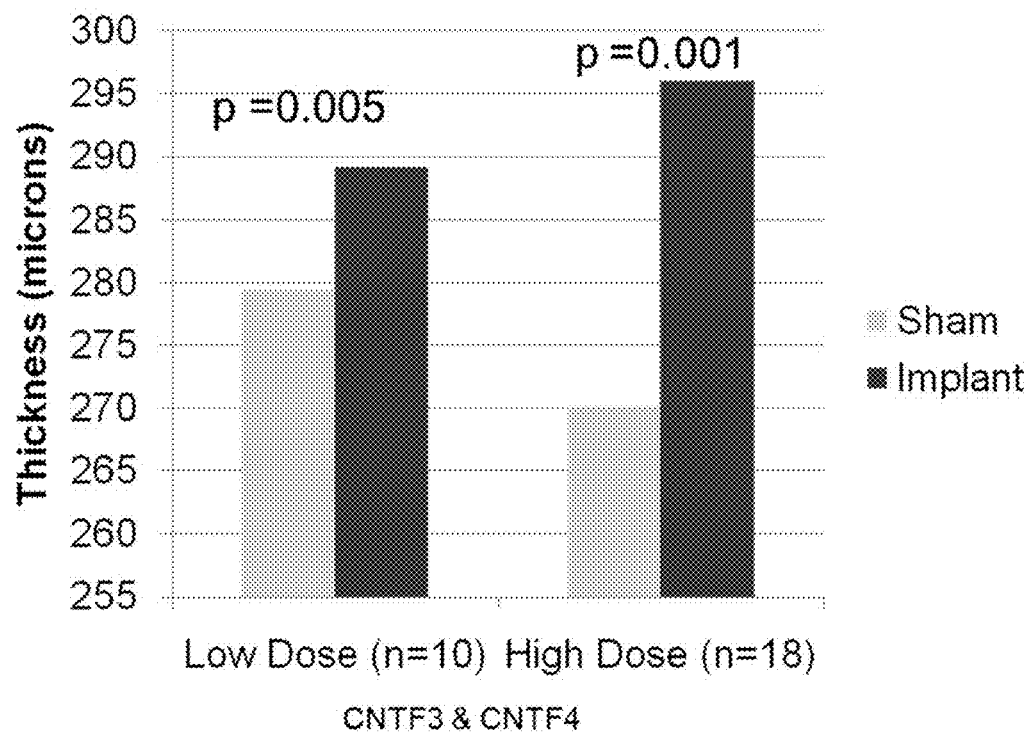
FIGS. 3A, 3B, 3C, and 3D are a series of graphs that depict the retinal thickness (FIGS. 3A, 3B) or the ellipsoid zone (EZ) width measurements of the retina (FIGS. 3C, 3D) in RP patients who received the CNTF-secreting device.
Figure 3B:
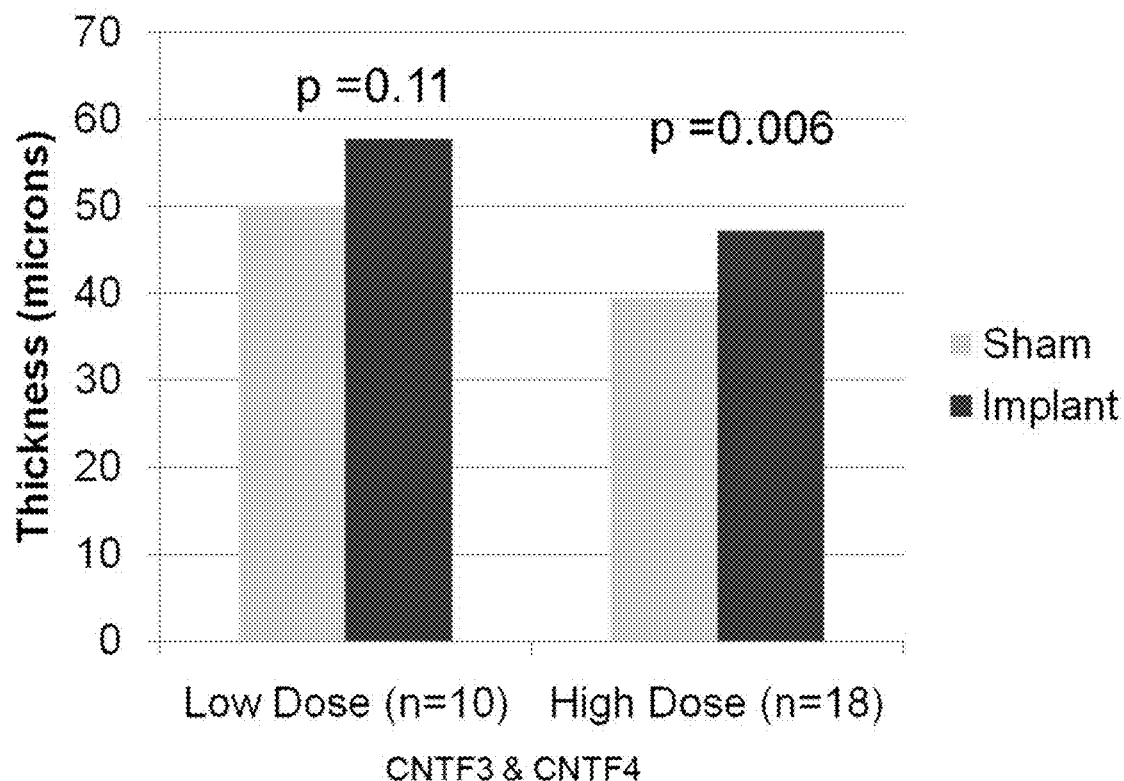

CNTF4 study participants also had ocular measurements performed with frequency domain optical coherence tomography (fdOCT) 12 months post-implant of either the low dose (5±0.8 ng/day) or the high dose (20±3.0 ng/day) CNTF-secreting device. FIG. 3A depicts the results of the fdOCT assessment. The study participants had increased retinal thickness in the eye receiving either the low or the high dose secreting device in comparison to the sham treated eye. The data demonstrate that there were significant (p<0.01) increases in retinal thickness for both the high dose and the lose dose study participants. The CNTF4 study participants also had the thickness for the outer nuclear layer (ONL) of the retina assessed 12 months post-implant by Spectralis OCT. (See FIG. 3B.).

The data demonstrate that there is a trend of increased thickness of the ONL in the low dose device recipients, and a significant difference in the thickness of the ONL in the high dose device recipients. The amount of the thickness increase was approximately 8 micrometers in both the low and high dose device recipients.

Figure 3C:
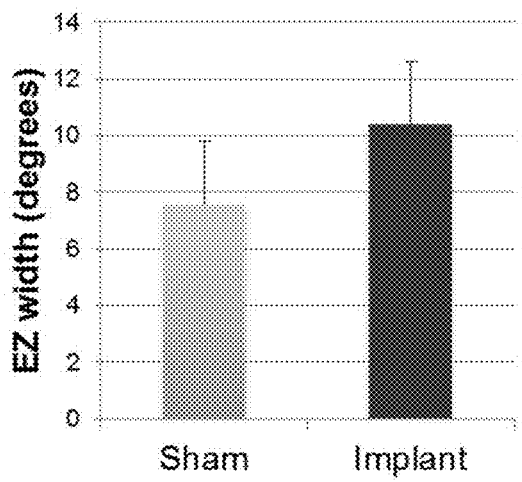
Figure 3D:
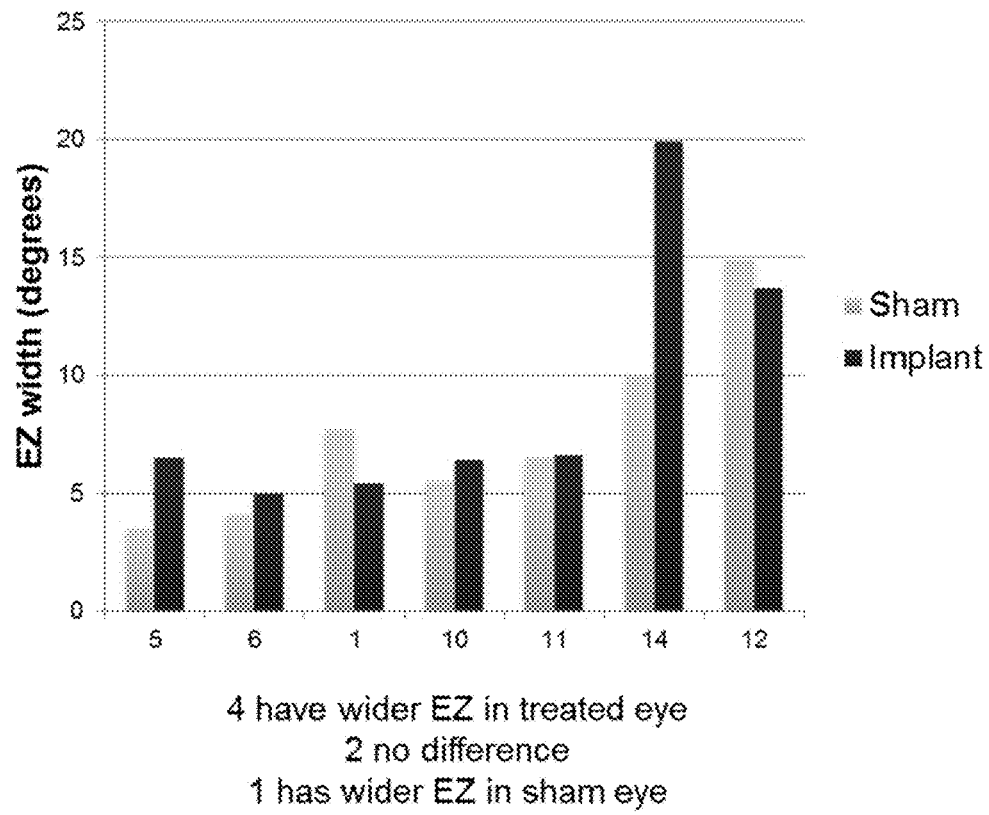

Ellipsoid zone (EZ) width measurements of the retina were performed at 72 months post-implant of the CNTF secreting device. The data for the EZ width measurements are presented in FIGS. 3C and 3D and indicate that participants that received an implant of the CNTF-secreting device had a thicker EZ in comparison to the sham treated eye. Thickness of the EZ is an often-used measure to track the progression of RP. The increased thickness of the EZ, in comparison to the width of the EZ in the sham treated eye, indicates that RP has a slower degenerative progression in the CNTF-device implanted eye.

Collectively, these data suggest: 1) there is evidence of increased outer retinal thickness by OCT out to 72 months after implant of the CNTF-secreting device; and 2) the increased outer retinal thickness is associated with a 1-line improvement in the visual acuity among the late RP patients.

Example 2

Glaucoma Clinical Trial

Patient Profile and Study Design

Glaucoma patients were recruited for a clinical trial in which the participants would receive a high dose CNTF-secreting device (20±3.0 ng/day). Inclusion and exclusion criteria for candidate participants are shown in Table 2. Importantly, in order to qualify as a study participant, candidates had to have: 1) clinical evidence of progressive retinal ganglion (RG) cell dysfunction and degeneration using both visual field and at least one structural modality; 2) residual visual field preservation, including best corrected visual acuity (BCVA); and 3) failure to contain glaucomatous progression with maximally tolerated reduction of intraocular pressure (TOP), or visual field defect affecting fixation, or subjective visual field loss affecting activities of daily living.

TABLE 2

Inclusion/Exclusion Criteria for the Glaucoma Study

| INCLUSION CRITERIA | EXCLUSION CRITERIA |
| --- | --- |
| must understand and sign the informed consent. | other corneal, lens, optic nerve or retinal disease causing vision loss |
| must be medically able to undergo ophthalmic surgery for the high dose CNTF-secreting device insertion and possible removal, as well as the testing required. | blind in one eye |
| diagnosis of glaucoma characterized by (a) clinical evidence of progressive RGC dysfunction and degeneration using both visual field and at least one structural modality; (b) residual visual field preservation including best-corrected visual acuity (BCVA) better than 20/100; (c) failure to contain glaucomatous progression with maximally tolerated reduction of intraocular pressure (IOP), OR visual field defect affecting fixation, but not reducing BCVA below 20/100 | requirement of acyclovir and/or related products during study |
| 18 years and older | receiving systemic steroids or other immunosuppressive medications |
| clinical evidence of progressive RGC dysfunction and degeneration using both visual field and at least one structural modality | pregnant or lactating |
| residual visual field preservation including BCVA | considered immunodeficient or has a known history of human immunodeficiency virus (HIV) |
| failure to contain glaucomatous progression with maximally tolerated reduction of IOP, OR visual field defect affecting fixation, or subjective visual field loss affecting activities of daily living | on chemotherapy, or a history of malignancy, UNLESS it was treated successfully 2 years prior to inclusion in the trial |

The patient profiles are summarized in Table 3. The BCVA of the study participants ranged from 20/25-20/100. The VF indices of the participants were MD −4.25 to −19.53. The worse eye of the study participant was chosen as the eye for device implantation.

TABLE 3

Patient Profile for the Glaucoma Study

| Ethnicity/Race | Male | Female |
| --- | --- | --- |
| Caucasian | 4 | 2 |
| Hispanic | 1 | 2 |
| African-American | 1 | 1 |

The study was designed to assess the safety of the implanted devices by counting the number of patients with adverse events including loss of vision, visual field, or retinal/optic nerve structure, and ocular complications including pain and inflammation. Secondary outcome measures included functional (e.g. assessment of vision, visual field, pattern electro-retinogram, and a visual field questionnaire) and structural efficacy (e.g. assessment of the nerve fiber layer and optic nerve topography).

Sustained Release CNTF-Secreting Device

The CNTF-secreting ECT device is detailed in Example 1, supra. Participants in the Glaucoma study only received the high dose (20±3.0 ng/day) CNTF-secreting device.

Implantation of the CNTF-Secreting Device

The device was implanted as detailed in Example 1, supra. The ARPE-19 containing, CNTF-secreting ECT device was inserted through the pars plana and secured to the scleral closure.

Post-Implant Patient Assessment

Figure 4:
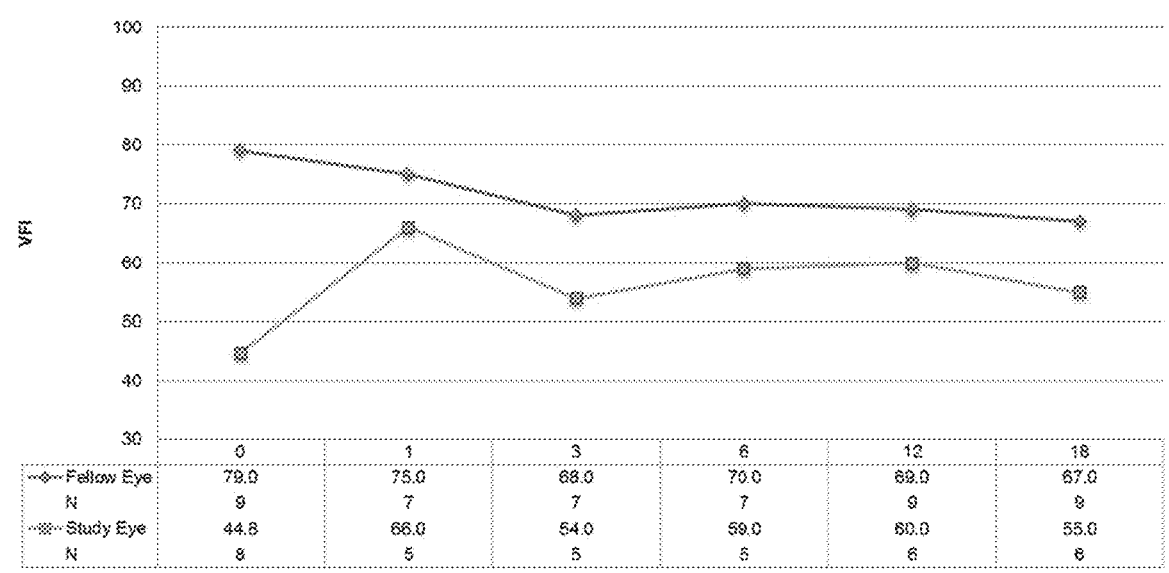
FIG. 4 is a graph that depicts the visual field index (VFI) in glaucoma patients that received a high dose CNTF-secreting ophthalmic ECT device (20±3.0 ng/day at implant) in one eye and received no treatment or a sham treatment in the other eye. The y-axis depicts VFI, and the x-axis depicts the assay time points and cohort identity.
Figure 5:
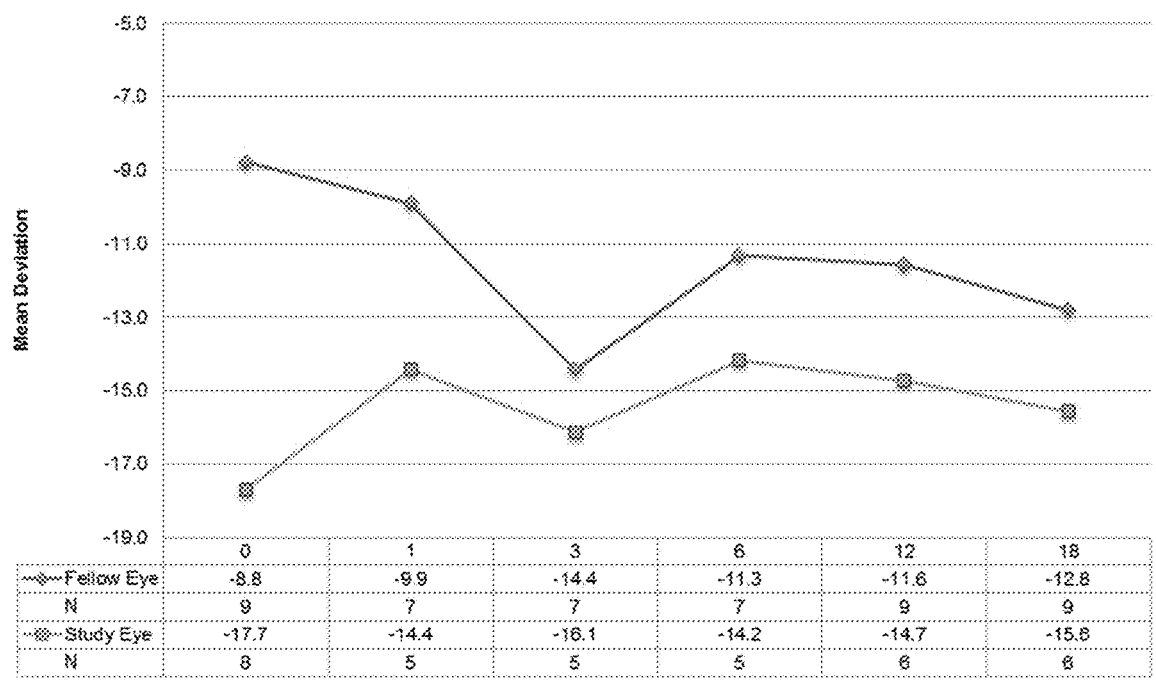
FIG. 5 is a graph that depicts the visual field mean deviation in glaucoma patients that received a high dose CNTF-secreting ophthalmic ECT device (20±3.0 ng/day at implant) in one eye and received no treatment or a sham treatment in the other eye. The y-axis depicts total deviation, and the x-axis depicts the assay time point and cohort identity.
Figure 6:
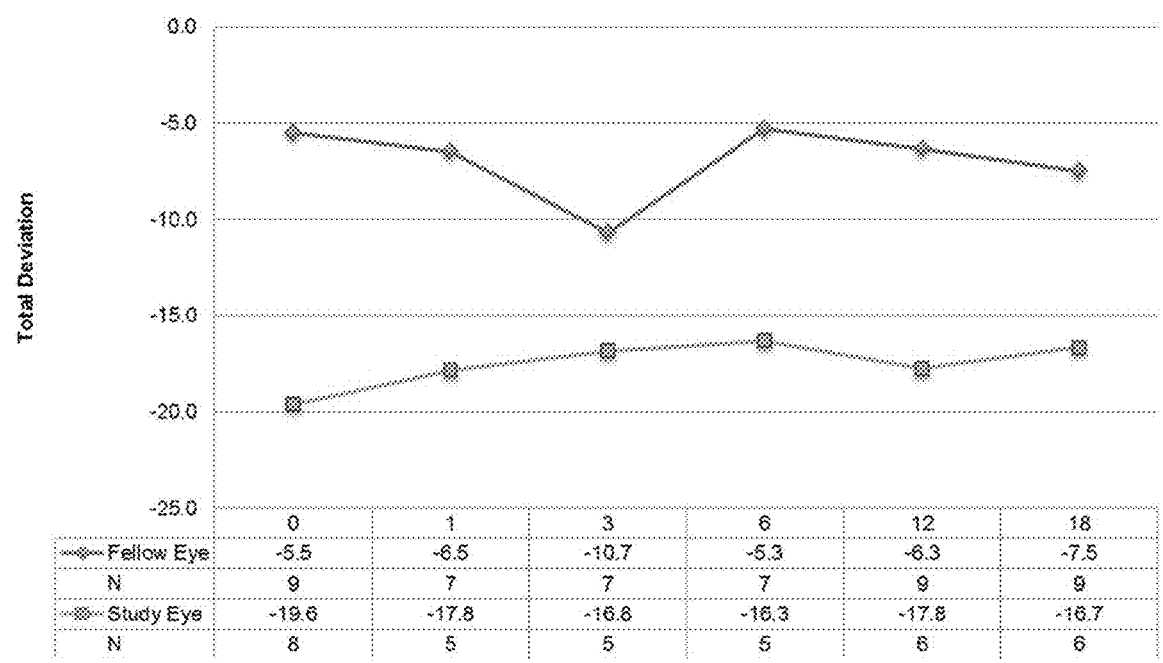
FIG. 6 is a graph that depicts the Garway-Heath Total Deviation of the central region in glaucoma patients that received a high dose CNTF-secreting ophthalmic ECT device (20±3.0 ng/day at implant) in one eye and received no treatment or a sham treatment in the other eye. The y-axis depicts total deviation, and the x-axis depicts the assay time point and cohort identity.
Figure 7:
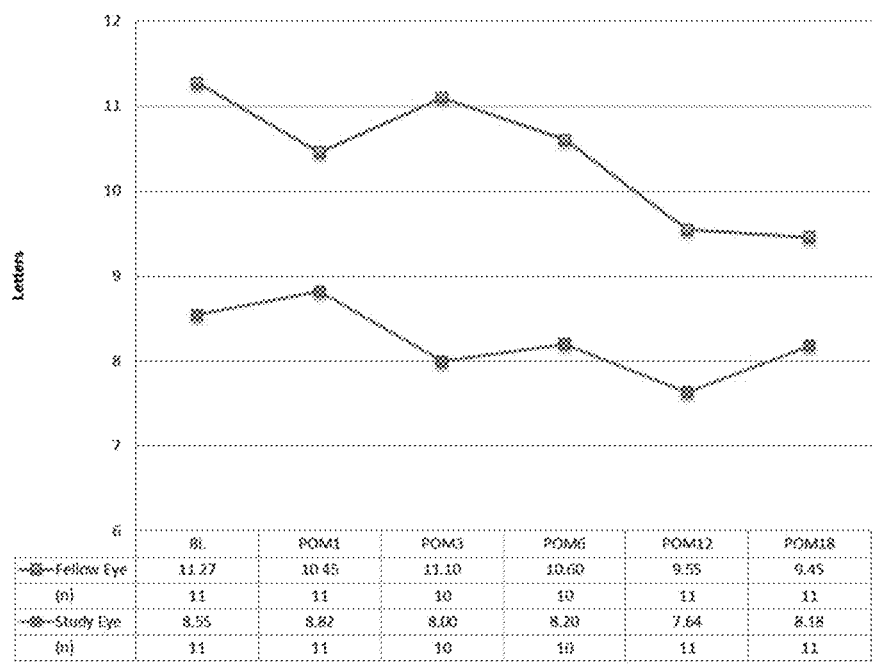
FIG. 7 is a graph that depicts the Pelli-Robson Contrast Sensitivity in glaucoma patients that received a high dose CNTF-secreting ophthalmic ECT device (20±3.0 ng/day at implant) in one eye, and received no treatment or a sham treatment in the other eye. The y-axis depicts letters discernable by the patient, and the x-axis depicts the assay time point and cohort identity.

The study participants maintained well-controlled intraocular pressures during the trial in both eyes (i.e. the study eye and the fellow eye). The visual field index (VFI) was assessed over an 18 month period following the implant of the CNTF-secreting device into the eye. FIG. 4 is a graph that depicts the VFI of study participants over an 18 month period following implant of the CNTF-secreting device. The data indicate that as early as one-month post-implant that there was detectable improvement in the VFI in the study eye. FIGS. 5 and 6 are a series of graphs that depict the visual field mean deviation in study participants over an 18 month period. The data indicate that there is improvement in the mean deviation of the study eye as early as one-month post-implant. Visual acuity assessments included the Pelli-Robson Contrast Sensitivity test. (See FIG. 7). These data indicate an improvement in the amount of letters identified by the study eye as early as one month post implant. Notably, these data indicate an improved central region associated with preserved contrast sensitivity in the study eye (i.e. the eye receiving the CNTF-secreting device).

Figure 8:
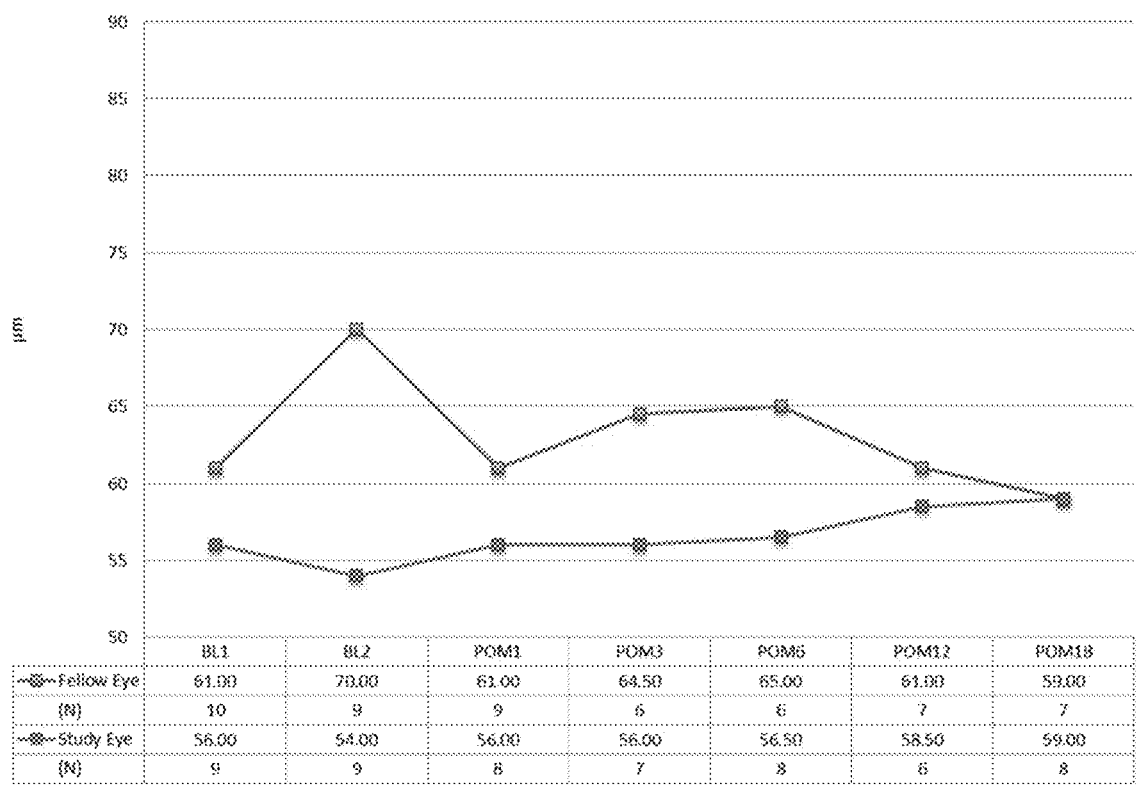
FIG. 8 is a graph that depicts the thickness of the ganglion cell complex in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 9:
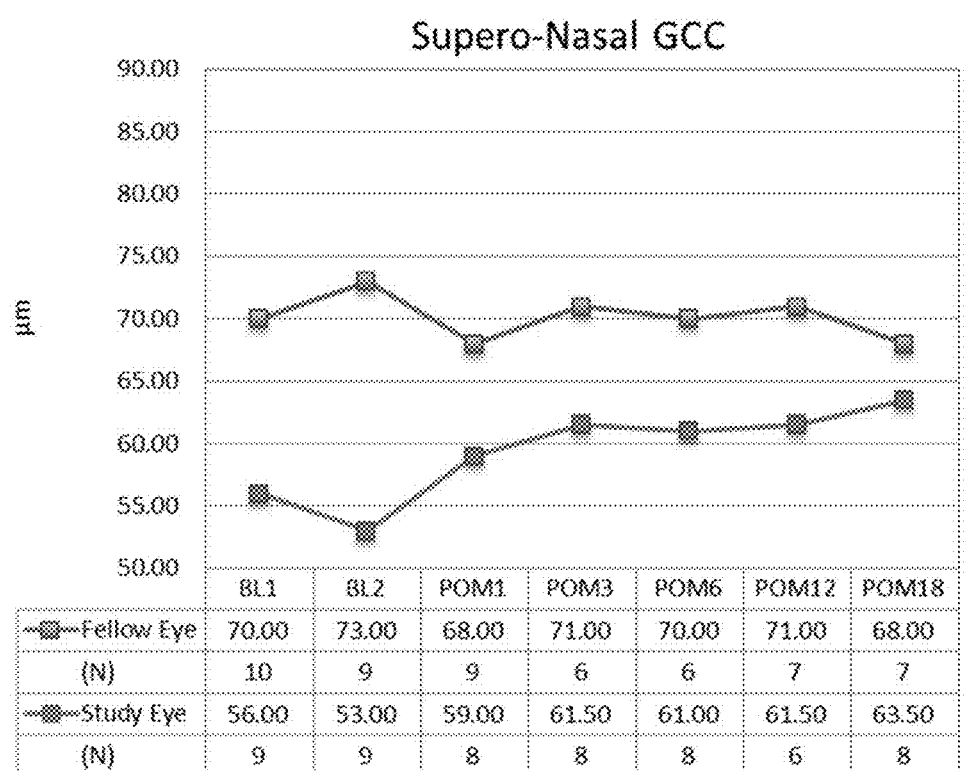
FIG. 9 is a graph that depicts the thickness of the ganglion cell complex in the supero-nasal region in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 10:
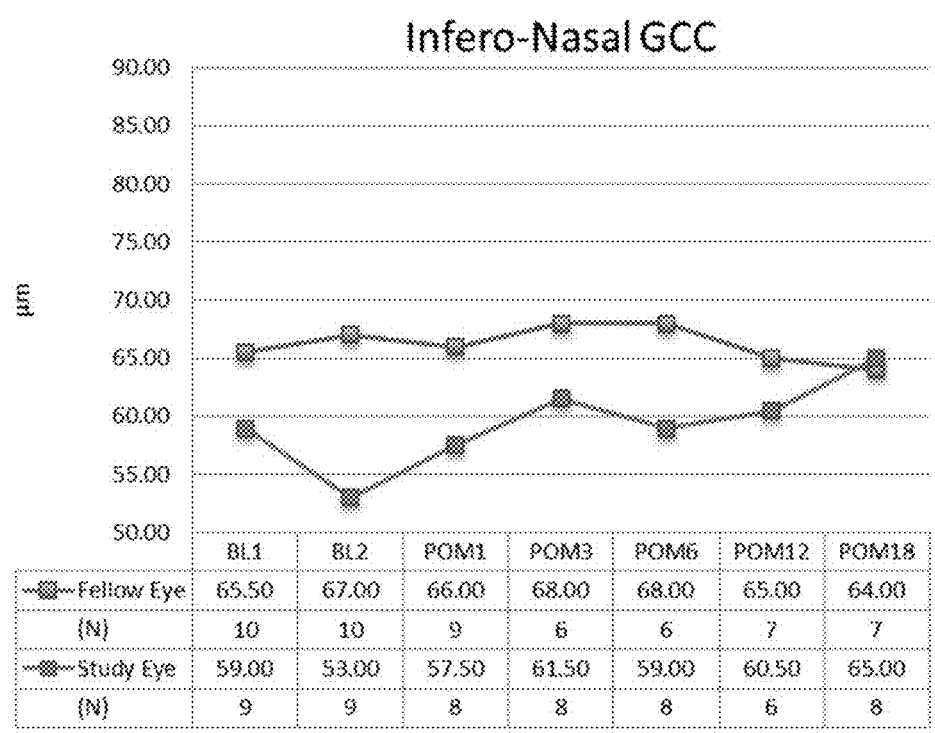
FIG. 10 is a graph that depicts the thickness of the ganglion cell complex in the infero-nasal region in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.

The ganglion cell complex associated with the supero-nasal and the infer-nasal sectors was assessed over an 18 month period. The data presented in FIG. 8 demonstrate a progressive increase in the thickness of the ganglion cell complex over the 18 month assessment period for the study eye. FIGS. 9 and 10 present measurements of the thickness of the supero-nasal and the infero-nasal ganglion cell complex (GCC), respectively, in study participants over an 18 month period. The data indicate a progressive thickening of the GCC over the 18 month assessment period and that the improvement in visual field acuity is associated with an improvement in the corresponding GCC.

Figure 11:
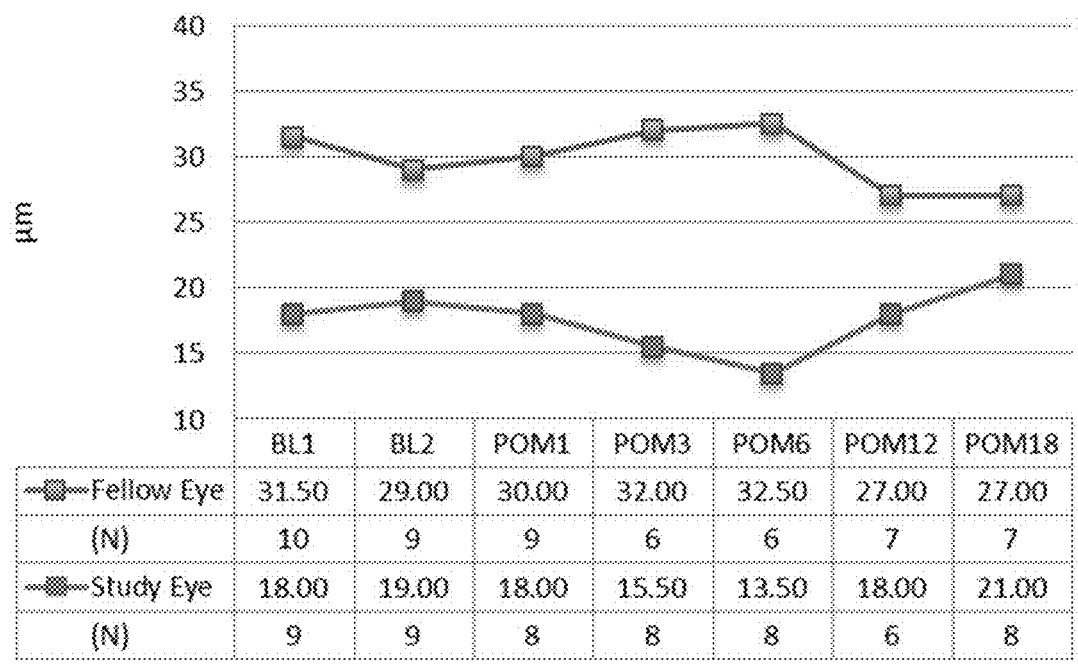
FIG. 11 is a graph that depicts the thickness of the supero-nasal macular nerve fiber layer in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 12:
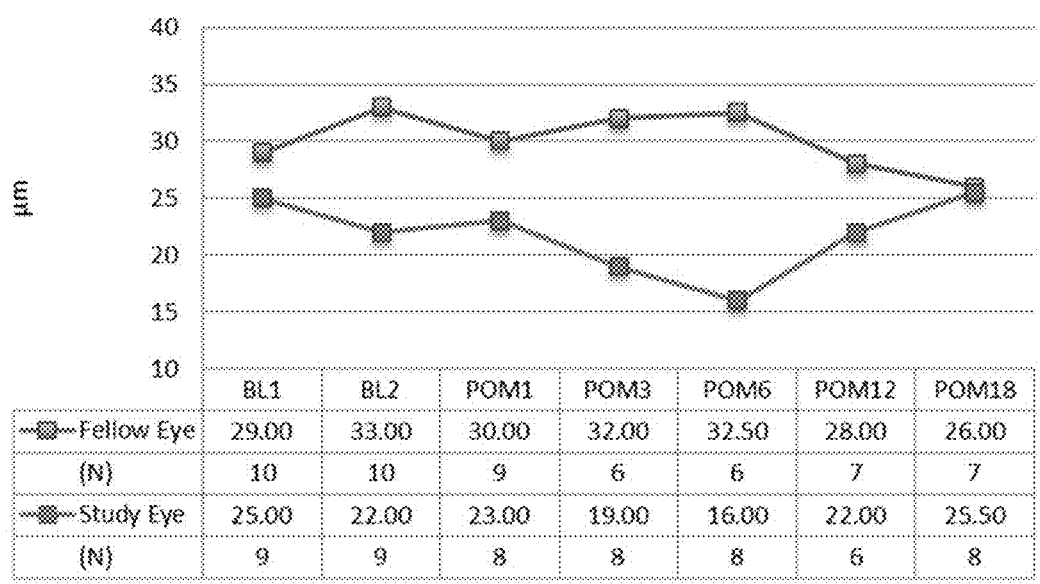
FIG. 12 is a graph that depicts the thickness of the infero-nasal macular nerve fiber layer in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 13:
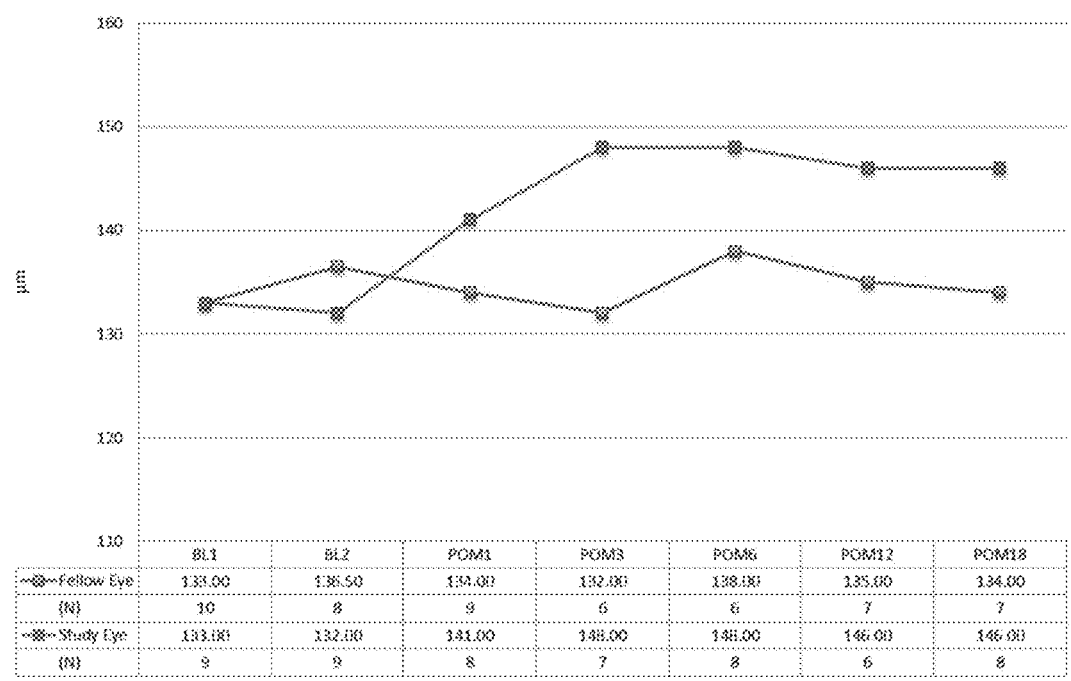
FIG. 13 is a graph that depicts thickness of the outer retina layer in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 14:
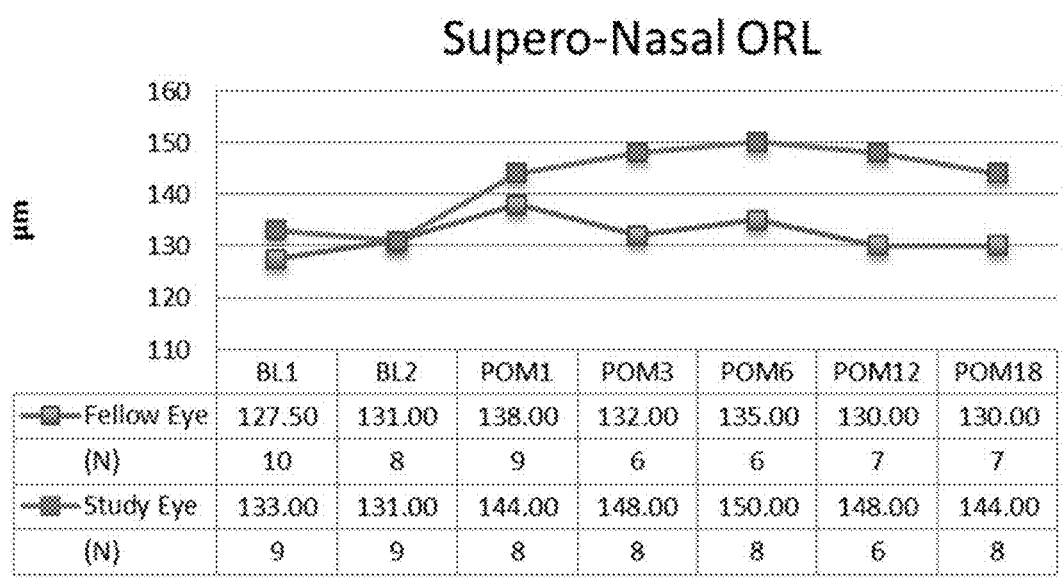
FIG. 14 is a graph that depicts the thickness of the supero-nasal outer retina layer in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 15:
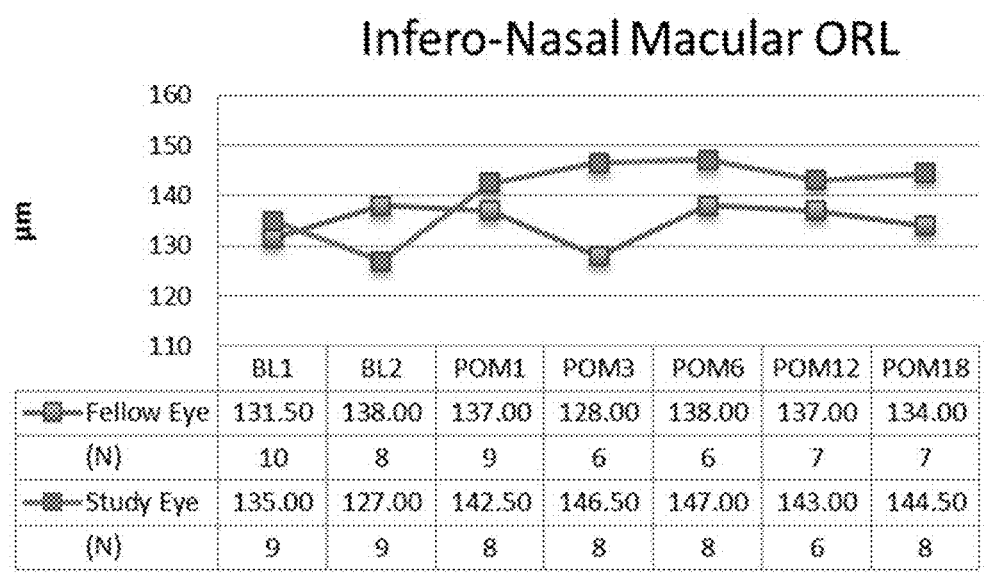
FIG. 15 is a graph that depicts the thickness of the infero-nasal macular ORL in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 16:
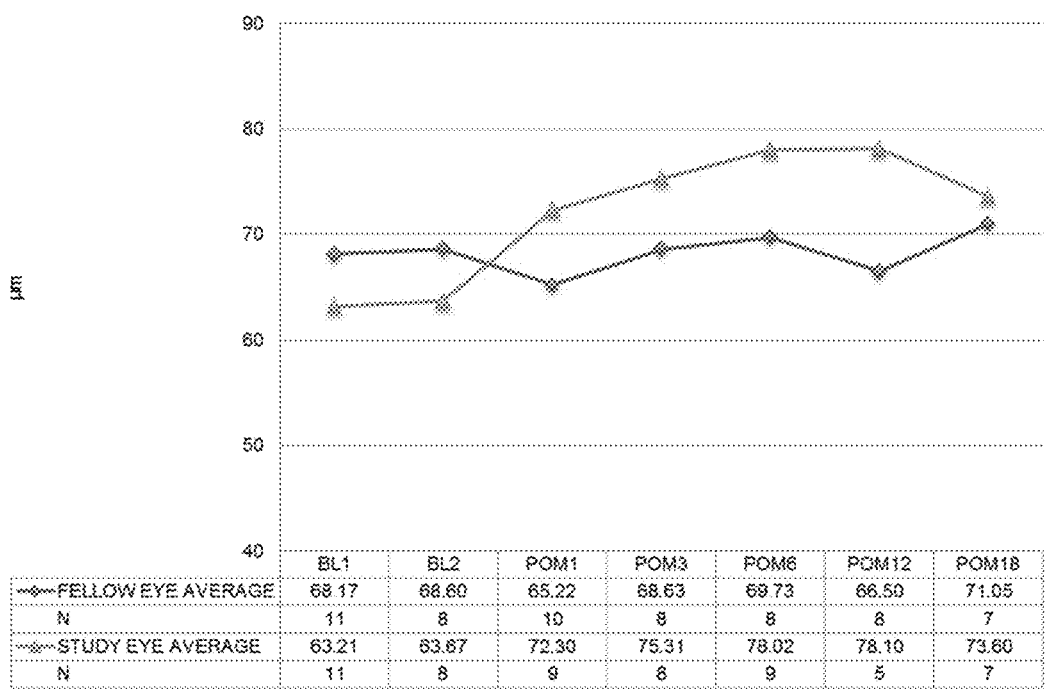
FIG. 16 is a graph that depicts the thickness of the retinal nerve fiber layer in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.
Figure 17:
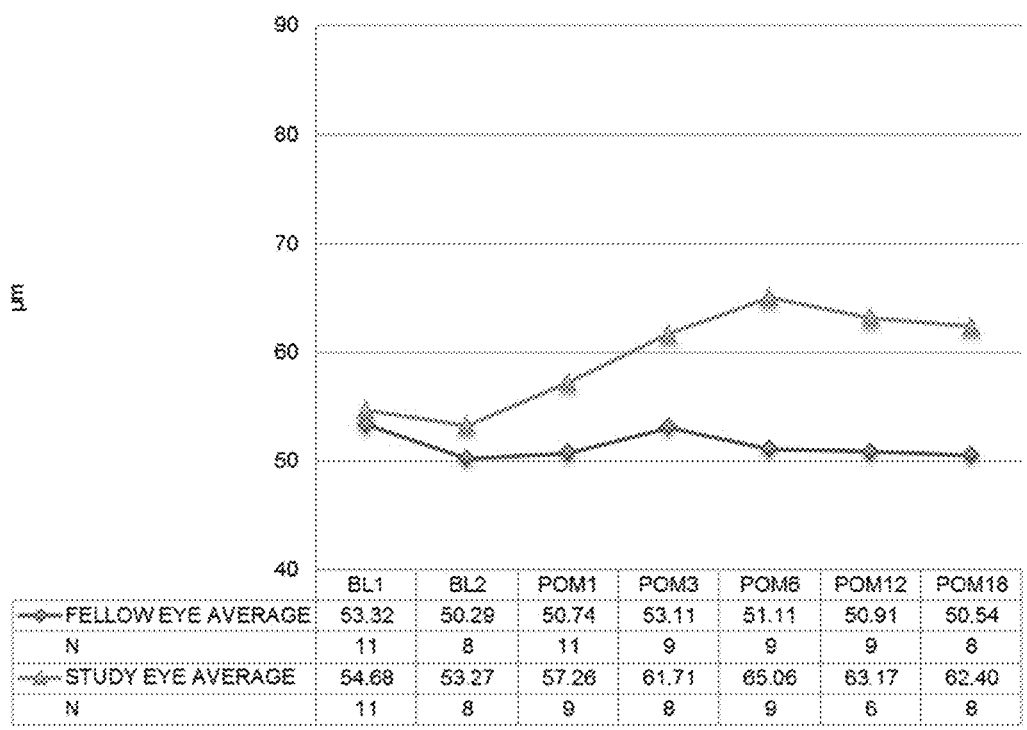
FIG. 17 is a graph that depicts the thickness of papillomacular bundle (temporal) fibers in glaucoma patients that received a high dose CNTF-secreting ophthalmic ECT device (20±3.0 ng/day at implant) in one eye and received no treatment or a sham treatment in the other eye. The y-axis depicts thickness in microns, and the x-axis depicts the assay time point and cohort identity.

The study also found evidence of increased nerve fiber layer thickness in study participants who had received the CNTF-secreting device implant. See FIGS. 11, 12 and 16. Additional data demonstrate that there is an improvement of the overall outer retina layer, supero-nasal outer retinal layer, and the infero-nasal macular outer retinal layer post implant of the CNTF-secreting device. See FIGS. 13, 14, and 15. Marked improvements were also noted in the thickness of the temporal nerve fiber layer (papillomacular bundle). See FIG. 17. FIG. 18 depicts the increasing thickness of the retinal nerve fiber layer in selected study participants in the study eye when compared to the sham treated eye.

Collectively, these data suggest: 1) an improvement in the visual field and preservation of contrast sensitivity in the CNTF treated eyes when compared with the better fellow eye; 2) the improvements in function are correlated with structural improvements in OCT thickening of the corresponding retinal nerve fiber layer, papillomacular bundle, ganglion cell complex and outer retinal layers; and 3) the structural and functional improvements are evident as early as 1 month post-implant of the CNTF-secreting device and persist to at least 18 months.

Example 3

Geographic Atrophy Trial

Patient Profile and Study Design

Geographic atrophy (Dry Age Related Macular Degeneration (AMD)) patients were recruited for this clinical trial in which the participants would receive a CNTF-secreting intraocular ECT device. The study was designed to be randomized, double-masked, sham controlled and performed in multiple research centers in the U.S. The study design included geographic atrophy patients that would either receive a low dose CNTF-secreting device, a high-dose CNTF-secreting device, or a sham treatment in a fellow eye. A total of 51 subjects were recruited for the study: 27 received the high dose device, 12 received the low dose device, and 12 received the sham treatment.

The primary outcome assessment was study participant best corrected visual acuity at 12 months post implant. Additional assessments performed included a safety assessment of study participants. The study was designed to last one year.

Sustained Release CNTF-Secreting Device

The CNTF-secreting device is detailed in Example 1 above. Participants in the geographic atrophy trial received either a low dose (5±0.8 ng/day), a high dose (20±3.0 ng/day) CNTF-secreting device, or a sham treatment.

Implantation of the CNTF-Secreting Device

The device was implanted as detailed in Example 1 above.

Post-Implant Patient Assessment

Patients were assessed for adverse events or eye disorders during follow-up examinations. See Table 4. The safety data indicates that adverse incidences were no more common among CNTF-secreting implant recipients when compared to those that received the sham procedures.

TABLE 4

Adverse Events/Eye Disorders in Geographic Atrophy Clinical Trial

| Adverse Events/Eye Disorders | High Dose (n = 27) | Low Dose (n = 12) | Sham (n = 12) |
|---|---|---|---|
| IOP Increase* | 2 (7.4%) | 2 (16.7%) | 3 (25%) |
| Eye Haemorrhage** | 2 (7.4%) | 1 (8.3%) | 1 (8.3%) |
| Photopsia | 2 (7.4%) | 1 (8.3%) | 0 (0.0%) |
| Miosis | 1 (3.7%) | 1 (8.3%) | 0 (0.0%) |
| Cataract | 1 (3.7%) | 0 (0.0%) | 0 (0.0%) |
| CNV | 0 (0.0%) | 0 (0.0%) | 1 (8.3%) |
| Iritis | 0 (0.0%) | 0 (0.0%) | 0 (0.0%) |
| Wound Leaks or Erosion | 0 (0.0%) | 0 (0.0%) | 0 (0.0%) |
| Endophthalmitis | 0 (0.0%) | 0 (0.0%) | 0 (0.0%) |
| Implant Extrusion | 0 (0.0%) | 0 (0.0%) | 0 (0.0%) |
| Retinal Detachment | 0 (0.0%) | 0 (0.0%) | 0 (0.0%) |

Figure 19:
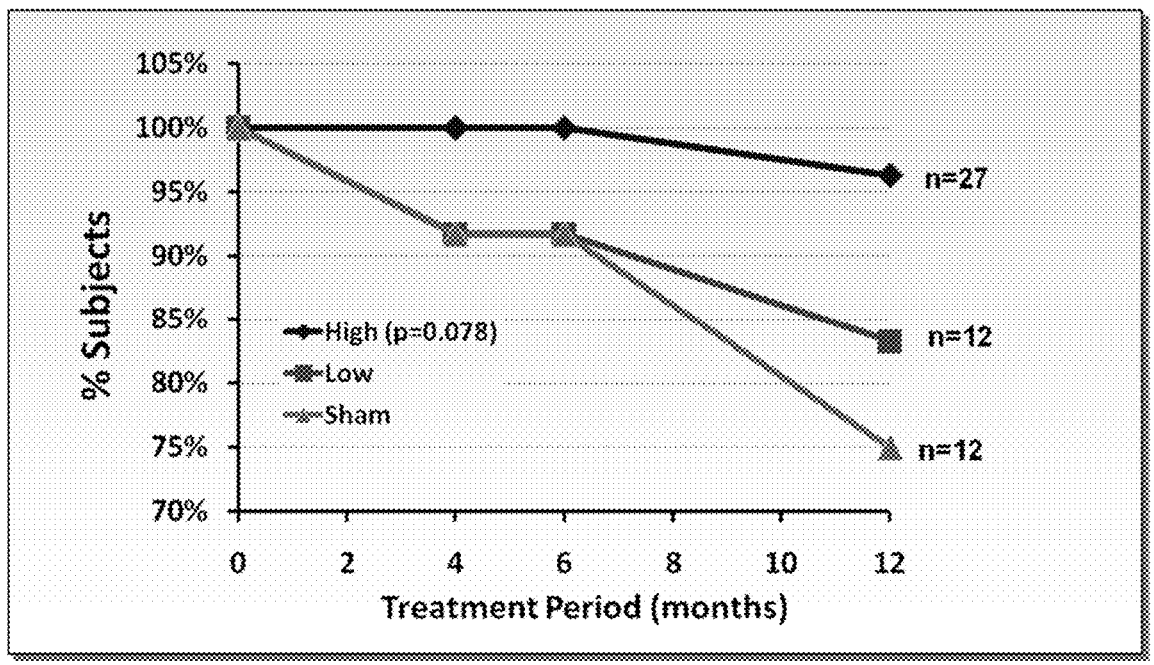
FIG. 19 is a graph that depicts the percentage of geographic atrophy patients who have lost less than fifteen letters from baseline over a twelve-month time period. The patients in this study either received a low dose (5±0.8 ng/day at implant) or a high dose (20±3.0 ng/day at implant) CNTF-secreting ophthalmic ECT device, or a sham treatment. The y-axis depicts the percentage of subjects that have lost fewer than fifteen letters from baseline, and the x-axis depicts the time the vision tests were performed post-implant of the ECT device.
Figure 20:
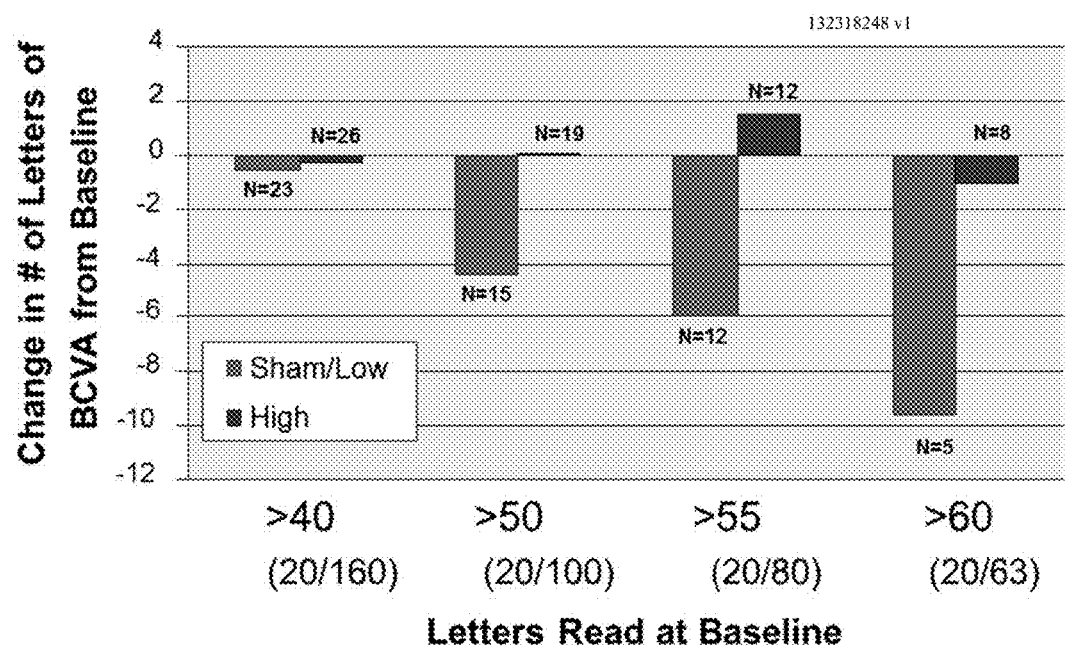
FIG. 20 is a graph that depicts the best corrected visual acuity (BCVA) of geographic atrophy patients that received either a sham or a low (5±0.8 ng/day at implant) CNTF-secreting ophthalmic ECT device in comparison to those geographic atrophy patients that received a high CNTF-secreting ophthalmic ECT device (20±3.0 ng/day at implant). The y-axis depicts the change in the amount of letters discernable by the patient, and the x-axis depicts the letters read at baseline, prior to implant of the ophthalmic ECT device.

*IOP increase (24-31 mmHg) usually lasted a few days to a few weeks and returned to normal at the next scheduled visit without medical intervention
**Occurred approximately 10 days after the procedure and recovered with no sequelae within a few weeks Participants were assessed for the number of letters lost over the baseline assessment (i.e. prior to implant) at 4 months, 6 months and 12 months post-implant of the CNTF-secreting device. This visual acuity test measured the number of letters the study participants were able to discern from an ETDRS eye chart. FIG. 19 depicts the percentage of subjects that have lost the ability to discern fewer than 15 letters over a 12 month period. The data indicate that a greater percentage of study participants that received either the low or the high dose secreting device lost fewer than 15 letters over the 12 month period when compared to the participants receiving the sham treatments. Importantly, only approximately 4% of study participants that received the high dose CNTF-secreting implant lost greater than 15 letters as compared to approximately 16% of study participants that received the low dose CNTF-secreting device and to approximately 25% of the participants that received a sham treatment. The high dose cohort of the study also showed greater vision stabilization in subjects with better baseline visual acuity. See FIG. 20 and Table 5 and Table 6.

TABLE 5

Subjects with Better Baseline Visual Acuity had Greater Vision Stabilization Following CNTF-Secreting Implant

|  | High Dose (n = 10) | Low/Sham (n = 9)* | P-Value |
|---|---|---|---|
| 4 Months | 0/10 | 1/9 |  |
| 6 Months | 0/10 | 2/9 |  |
| 12 Months | 0/10 | 4/9 | P = 0.033 |

*Low dose (3) is 50% MED, sham (6) subjects receive external suture only

TABLE 6

High Dose Subjects Who Had Better Baseline Visual Acuity Showed Greater Vision Stabilization Following CNTF-Secreting Implant

|  | High Dose (n = 10) | Low/Sham (n = 9)* | P-Value |
|---|---|---|---|
| Baseline Mean | 62.6 (4.02) | 61.7 (3.6) |  |
| 12 Months Mean | 63.4 (4.8) | 52 (11.67) |  |
| Change from Baseline | 0.8 (5.36) | −9.7 (13.04) | P = 0.0315 |

*Low dose (3), 50% MED, and sham (6) subjects receive external suture only

Study participants were also screened for geographic atrophy lesion size at 12 months, post-CNTF-device implant. The data show that those subjects that had received either the low or the high dose CNTF-secreting implant had less progression in the sizes of the geographic atrophy lesion in comparison to the sham treated participants. (See Table 7).

TABLE 7

Progression of GA Lesion Size at 12 months Post-Implant of The CNTF-Secreting ECT Device

|  | High Dose (N = 23) | Low Dose (N = 10) | Sham (N = 11) |
|---|---|---|---|
| Baseline mean (mm$^2$) | 9.84 | 11.41 | 9.84 |
| Mean Change from Baseline (mm$^2$) | +2.03 | +2.19 (1.87) | +2.42 |

Collectively, these data suggest that the implant of either the high dose or the low dose CNTF-secreting device has beneficial effects for the treatment of geographic atrophy. Furthermore, the high dose CNTF-secreting devices have a greater impact in terms of maintaining, and lessening the progression of the disease as compared to both the low and the sham treatments.

Example 4

Explanted Device Characteristics

The study participants in the RP, glaucoma and the geographic atrophy studies were all given the option of having the CNTF-secreting device explanted upon completion of the study. Notably, few participants elected to have the devices removed at the end of the trial. One of the reasons given for choosing not to explant the device is that the device continues to have beneficial effects.

To assess whether the devices continued to secrete CNTF after the study periods, data were collected from explanted devices at 6, 12, 18 and 24 months post-implant. Immediately upon removal of the device, the device was submerged in Endo-SFM conditioned medium (GIBCO BRL, Gaithersburg, Md.) at 37° C., 5% $CO_2$, and 95% humidity for 24 hours, and the rate of CNTF was determined. The rate of secreted CNTF was determined by ELISA.

The results of ELISA analysis of the culture medium are shown in Table 8. The mean daily CNTF release rate for the devices was determined to be 0.19±0.12 ng CNTF/day for the low dose device, and the mean daily CNTF release rate was 1.6±0.1 ng CNTF/day for the high dose device.

TABLE 8

Amount of CNTF Secreted from CNTF-Secreting Device Pre-Implant VS. Post-Implant

|  | Low Dose CNTF-Secreting ECT Device | High Dose CNTF-Secreting ECT Device |
|---|---|---|
| Pre-Implant | 5.0 ± 0.8 ng CNTF/day | 20.0 ± 3.0 ng CNTF/day |
| 6 Months Post-Implant | 0.28 ± 0.07 ng CNTF/day | 2.1 ± 0.5 ng CNTF/day |
| 24 Months Post-Implant | 0.15 ± 0.17 ng CNTF/day | 1.1 ± 0.5 ng CNTF/day |

Pharmacokinetic modeling indicated that the mean residence time (MRT) of CNTF (i.e. the time at which the devices are predicted to produce approximately 36% of the secreted amounts of CNTF when compared to the 6 month CNTF secretion amount) for the low dose device would be 30 months, and the CNTF for the high dose device would be 47 months.

Collectively, these data surprisingly show that the devices continued to produce CNTF over prolonged periods of time well in excess of the 12 or 24 month study design periods. Moreover, these data also suggest that maintaining the implants in the patients' eyes for longer periods of time may be beneficial in the treatment of ophthalmic disorders such as RP, glaucoma and/or geographic atrophy.

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

What is claimed is:

1. A method of improving optic nerve regeneration; preserving or improving the ganglion cell complex, the thickness of the outer retinal layer, or both the ganglion cell complex and the thickness of the outer retinal layer; or preserving or improving the retinal fiber layer in a patient in need thereof comprising: implanting into an eye of the patient a biocompatible capsule comprising
   a) a core comprising $0.5$-$1 \times 10^6$ ARPE-19 cells that are genetically engineered to secrete a therapeutically effective amount of CNTF upon implantation, wherein the therapeutically effective amount is between 0.1 and 20 ng/day;
   b) a semi-permeable membrane surrounding the core, wherein the membrane has a molecular weight cut off of 50 kD, permits the diffusion of the CNTF therethrough, and is between 90 and 120 µm thick; and
   c) a matrix disposed within the semi-permeable membrane, wherein said matrix comprises monofilaments that are twisted into a yarn that is in non-woven strands, wherein the cells are distributed thereon, and wherein the monofilaments comprise polyethylene terephthalate (PET) fibers that comprise 40-85% of the internal volume of the capsule;
   wherein said biocompatible capsule produces 0.6-5.0 ng/day of CNTF for at least 12 months post implantation, and
   wherein the capsule is configured as a hollow fiber having an internal diameter of 0.9-1.2 mm and a length of 4-11 mm.

2. The method of claim 1, wherein the biocompatible capsule produces 0.6-5.0 ng/day of CNTF for at least 2 years post implant.

3. The method of claim 1, wherein the method preserves or improves visual field sensitivity, contrast, sensitivity, Garway-Heath total deviation, or any combinations thereof.

4. The method of claim 3, wherein the preservation or improvement of visual field sensitivity or contrast sensitivity corresponds with preservation or improvement of the anatomical structure of the retina.

5. The method of claim 1, wherein said capsule is implanted in the vitreous, in the aqueous humor, in the periocular space, in the anterior chamber, in the posterior chamber, or in the Subtenon's space.

6. The method of claim 1, wherein the biocompatible capsule is anchored to an ocular structure following implantation.

7. The method of claim 1, wherein the semi-permeable membrane comprises a permselective, immunoprotective membrane.

8. The method of claim 7, wherein the semi-permeable membrane has a median pore size of 100 nm.

9. The method of claim 1, wherein one or more ARPE-19 cells in the core are genetically engineered to secrete at least one additional biologically active molecule.

* * * * *